(12) United States Patent
Song et al.

(10) Patent No.: US 11,298,547 B2
(45) Date of Patent: Apr. 12, 2022

(54) FLUID STATUS DETECTION FROM A CARDIAC ELECTRICAL SIGNAL AND IMPEDANCE SIGNAL

(71) Applicant: Medtronic, Inc., Minneapolis, MN (US)

(72) Inventors: Zhendong Song, Medina, MN (US); Todd M. Zielinski, Ham Lake, MN (US); Brian B. Lee, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 271 days.

(21) Appl. No.: 16/521,963

(22) Filed: Jul. 25, 2019

(65) Prior Publication Data

US 2020/0030612 A1    Jan. 30, 2020

Related U.S. Application Data

(60) Provisional application No. 62/703,968, filed on Jul. 27, 2018.

(51) Int. Cl.
*A61B 5/352* (2021.01)
*A61N 1/365* (2006.01)
(Continued)

(52) U.S. Cl.
CPC ........ *A61N 1/36585* (2013.01); *A61B 5/0031* (2013.01); *A61B 5/1116* (2013.01); *A61B 5/283* (2021.01); *A61B 5/352* (2021.01); *A61B 5/4875* (2013.01); *A61B 5/7221* (2013.01); *A61B 5/0537* (2013.01); *A61B 5/0538* (2013.01); *A61B 2560/0214* (2013.01); *A61B 2560/0223* (2013.01)

(58) Field of Classification Search
CPC .... A61N 1/36585; A61B 5/352; A61B 5/283; A61B 5/0031; A61B 5/1116; A61B 5/4875; A61B 5/7221; A61B 5/0537; A61B 5/0538; A61B 2560/0214; A61B 2560/0223
See application file for complete search history.

(56) References Cited

U.S. PATENT DOCUMENTS 5,507,782 A    4/1996  Kieval et al.
6,044,297 A    3/2000  Sheldon et al.
(Continued)

OTHER PUBLICATIONS (PCT/US2019/043597) PCT Notification of International Search Report, dated Nov. 10, 2019, 3 pages.
(Continued)

*Primary Examiner* — Ankit D Tejani
*Assistant Examiner* — Joshua Brendon Solomon

(57) ABSTRACT

A medical device is configured to generate fluid status signal data of a patient by determining impedance metrics from an impedance signal, determining cardiac electrical signal amplitudes from a cardiac electrical signal and determining a calibration relationship between the impedance metrics and cardiac electrical signal amplitudes. The medical device generates a fluid status signal data by adjusting cardiac electrical signal amplitudes according to the determined calibration relationship. The fluid status signal data may be displayed or monitored for detecting a change in the patient's fluid status.

46 Claims, 11 Drawing Sheets

(51) Int. Cl.
  *A61B 5/11* (2006.01)
  *A61B 5/00* (2006.01)
  *A61B 5/283* (2021.01)
  *A61B 5/0537* (2021.01)
  *A61B 5/0538* (2021.01)

(56) References Cited

U.S. PATENT DOCUMENTS

| | | |
|---|---|---|
| 6,931,272 B2 | 8/2005 | Burnes |
| 6,978,171 B2 | 12/2005 | Goetz et al. |
| 7,778,709 B2 | 8/2010 | Gollasch et al. |
| 7,986,994 B2 | 7/2011 | Stadler et al. |
| 8,219,198 B2 | 7/2012 | Gollasch et al. |
| 8,278,220 B2 | 10/2012 | Holtermann |
| 8,428,717 B2 | 4/2013 | Wang et al. |
| 8,532,785 B1 | 9/2013 | Crutchfield et al. |
| 8,972,005 B2 | 3/2015 | Rasmussen et al. |
| 9,197,173 B2 | 11/2015 | Denison et al. |
| 9,855,414 B2 | 1/2018 | Marshall et al. |
| 2004/0220632 A1* | 11/2004 | Burnes ............ A61B 5/366 607/9 |
| 2009/0012416 A1 | 1/2009 | Belalcazar et al. |
| 2014/0276151 A1* | 9/2014 | Xi ............ A61B 5/287 600/508 |
| 2015/0306375 A1 | 10/2015 | Marshall et al. |

OTHER PUBLICATIONS

Medtronic Carelink® Model 2090 Programmer Reference Manual, Medtronic, Inc. Minneapolis Minnesota, USA, 2013.

* cited by examiner

FLUID STATUS DETECTION FROM A CARDIAC ELECTRICAL SIGNAL AND IMPEDANCE SIGNAL

TECHNICAL FIELD

This disclosure relates to an implantable medical device for producing a fluid status signal of a patient using a cardiac electrical signal and an impedance signal while reducing drain on a power source in the implantable medical device.

BACKGROUND

Changes in fluid status can indicate whether a patient is experiencing worsening medical condition that may result in hospitalization. Hypervolemia or "fluid overload" is the condition of excess intravascular or extravascular fluid and can lead to edema, the collection of fluid in the cavities or tissues of the body such as pulmonary edema, which occurs commonly in congestive heart failure patients. Hypovolemia is a decreased volume of fluid in the vascular system and occurs with dehydration, traumatic injury, or over-diuresis among other conditions. Changes in fluid status can occur in a variety of diseases or conditions, including heart failure, liver disorders, peripheral vascular disease, kidney dysfunction and other medical conditions. Assessing a patient's fluid status is a challenge to medical practitioners. Early detection of a change in fluid status may allow early medical intervention and treatment and prevent or shorten hospitalizations.

Impedance of body tissues exposed to an applied electrical current (or voltage signal) produces a voltage potential (or induced current) across an electrode vector. Tissue impedance decreases with increasing fluid content. Impedance measurements may be performed by applying a drive current signal to an electrode pair and recording the voltage developed across the electrode pair. The known current and recorded voltage is related to the tissue impedance according to Ohm's Law. Impedance measurements have been used or proposed for use in patient monitoring for conditions such as pulmonary edema and cardiac volume.

SUMMARY

The techniques of this disclosure generally relate to generating a fluid status signal of a patient using a combination of an impedance signal and a cardiac electrical signal for detecting changes in the fluid status of the patient. Amplitudes of cardiac events, such as R-waves, may be correlated to body tissue impedance, which increases or decreases with decreasing or increasing fluid content, respectively. A medical device operating according to the techniques disclosed herein determines a calibration relationship between impedance metrics determined from an impedance signal and amplitudes determined from a cardiac electrical signal for use in the calibrating cardiac electrical signal amplitudes for generating a fluid status signal of a patient.

In one example, the disclosure provides a medical device including a sensing circuit configured to receive a cardiac electrical signal via electrodes coupled to the medical device, an impedance sensing circuit configured to apply a drive signal to electrodes coupled to the medical device and sense a resultant impedance signal, a telemetry circuit configured to transmit fluid status data to another medical device, and a control circuit coupled to the sensing circuit, the impedance sensing circuit and the telemetry circuit. The control circuit is configured to determine impedance metrics from the impedance signal and determine amplitudes from the cardiac electrical signal. The control circuit determines a calibration relationship between the impedance metrics and the amplitudes of the cardiac electrical signal. The control circuit generates fluid status signal data by determining and adjusting cardiac electrical signal amplitudes according to the determined calibration relationship. The control circuit may control the telemetry circuit to transmit the fluid status signal data to another medical device for displaying the fluid status signal data.

In another example, the disclosure provides a method performed by a medical device. The method includes determining impedance metrics from an impedance signal resulting from a drive signal applied to electrodes coupled to the medical device and determining amplitudes of a cardiac electrical signal received by a sensing circuit via electrodes coupled to the medical device. The method further includes determining a calibration relationship between the impedance metrics and the amplitudes of the cardiac electrical signal and generating fluid status signal data by determining and adjusting cardiac electrical signal amplitudes according to the determined calibration relationship. The method may include transmitting the fluid status signal data to another medical device for displaying the fluid status signal data.

In yet another example, the disclosure provides a non-transitory computer-readable medium storing a set of instructions which when executed by a control circuit of a medical device, cause the medical device to determine impedance metrics from an impedance signal resulting from a drive signal applied to electrodes coupled to the medical device and determine amplitudes from a cardiac electrical signal received by a sensing circuit via electrodes coupled to the medical device. The instructions further cause the medical device to determine a calibration relationship between the impedance metrics and the amplitudes of the cardiac electrical signal and generate fluid status signal data by determining and adjusting cardiac electrical signal amplitudes according to the determined calibration relationship. The instructions may further cause the medical device to transmit the fluid status signal data to another medical device for displaying the fluid status signal data.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
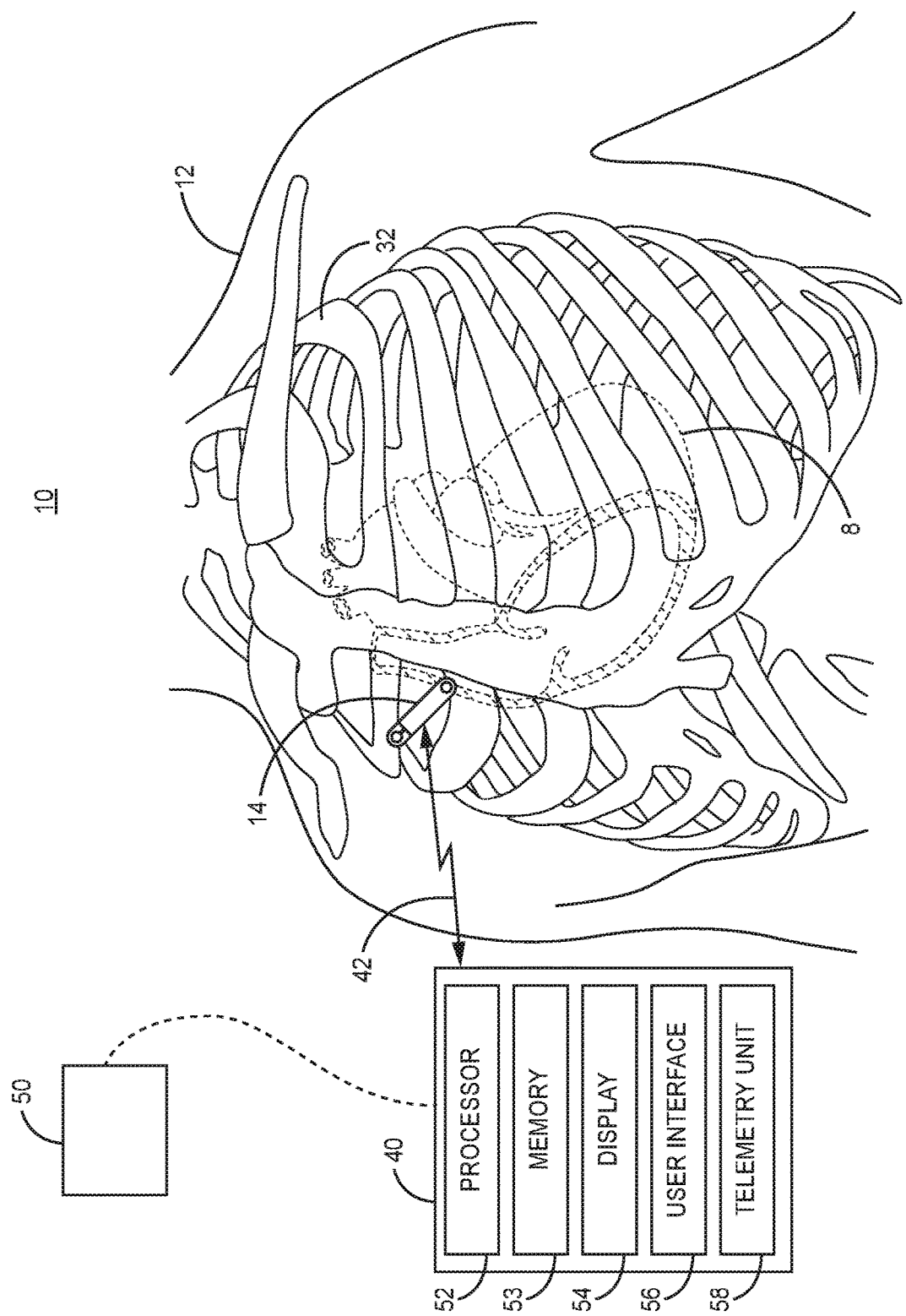
FIG. 1 is a conceptual diagram of a patient monitoring system including an implantable fluid status monitor and an external device.

A medical device and techniques for monitoring a patient's fluid status are disclosed herein. The term "fluid status" refers to a relative change of fluid within body tissue, including intravascular fluid and extra-vascular fluid. As such, an increased fluid status may indicate a hypervolumic condition or edema, and a decreased fluid status may indicate a hypovolemic condition or dehydration. In some cases, a change in fluid status may indicate a change in the patient's ability to regulate movement of fluid in the body, e.g., in response to body posture changes. As used herein, the term "monitoring" in regard to a patient's fluid status includes generating fluid status signal data by determining tissue impedance metrics and cardiac electrical signal amplitudes at multiple time points for producing a fluid status signal. The fluid status monitoring may further include transmitting the generated fluid status signal data to a device including a display unit for generating a display of the fluid status signal for observation by medical personnel. The fluid status monitoring may further include comparing the fluid status signal to one or more thresholds for detecting a fluid status change and generating an alert and/or adjusting or delivering a therapy (by the same or another medical device receiving the alert).

Impedance measurements are correlated to fluid present in body tissue and generally require a drive signal, typically having a known current amplitude, applied to an electrode pair in contact with body tissue. Application of the impedance drive current poses a relatively high power burden on the system. Depending on the desired frequency of impedance measurements performed for fluid status monitoring, application of the impedance drive current may deplete a limited power supply of the medical device, e.g., a battery-powered implantable medical device, relatively quickly, reducing the functional life of the medical device for fluid status monitoring and/or other device functions.

The heart generates an electrical signal, referred to herein as a "cardiac electrical signal," which can be recorded as an electrocardiogram (ECG) or intracardiac electrogram (EGM). The heart is effectively a current source. Accordingly, changes in the voltage amplitude of the cardiac electrical signal at a particular point in the cardiac cycle over time may serve as a voltage measurement that is at least in part a response to the current source of the heart. Changes in the voltage amplitude of a particular point in the cardiac cycle, e.g., the peak amplitude of the R-wave, may indicate a change in impedance of the heart tissues and any tissues between the heart and the recording electrodes. Using the heart as the "current source" reduces the power burden for monitoring changes in impedance for fluid status monitoring compared to using a drive current applied by the medical device. In examples described below, the amplitude of a cardiac electrical signal is used in combination with impedance measurements obtained using an applied drive current signal for producing a fluid status signal for monitoring the fluid status of a patient. This method of combining cardiac electrical signal amplitudes with impedance measurements for monitoring a patient's fluid status allows fluid status monitoring to be performed more frequently and/or with greater power efficiency compared to monitoring fluid status based on impedance measurements alone.

In the various examples presented herein, fluid status monitoring is performed by a monitoring device or a device configured to both monitor fluid status (and optionally other physiological signals) and deliver a therapy. Examples include devices configured to deliver electrical stimulation pulses to the patient's heart, e.g., a pacemaker or an implantable cardioverter defibrillator (ICD). However, it is to be understood that the fluid status monitoring techniques disclosed herein may be implemented in other types of medical devices, such as a drug delivery device, a ventricular assist device that includes a blood pump, a neurostimulator or other therapy delivery devices. Furthermore, the examples presented herein relate to implantable medical devices; however, aspects of the fluid status monitoring techniques may be implemented in external devices which may include wearable devices (e.g. GARMIN™ watch, APPLE™ WATCH, etc.) and/or bedside monitoring devices, (e.g. smart phone, etc.), which may be battery powered. The wearable or bedside monitoring devices automatically acquire data sensed from any implantable and/or external medical device through any suitable communication means. Exemplary communication means can include BLUETOOTH™, tissue conduction communication (TCC), etc. Additionally, the time of day (e.g. nighttime or when the patient typically sleeps) in which a person's posture changes can be acquired from the medical device. For example, when a person is exhibiting a resting heart rate at night and moves from a flat position (180 degrees) to a more elevated position (e.g. up to 30 degrees etc. by propping themselves up on a pillow), it may be due to relieving congestion in his or her lungs. Congestion typically worsens at the end of the person's day and is preparing to sleep. A person may be congested for a variety of reasons. One reason is that the patient may be experiencing worsening congestive heart failure (CHF). If the patient continues to experience congestion for extended periods of times (e.g. months etc.) his cardiac condition (CHF) is likely worsening. Worsening CHF can result in the implantable medical device to begin monitoring another parameter and/or increase the frequency of monitoring one or more parameters.

Figure 2:
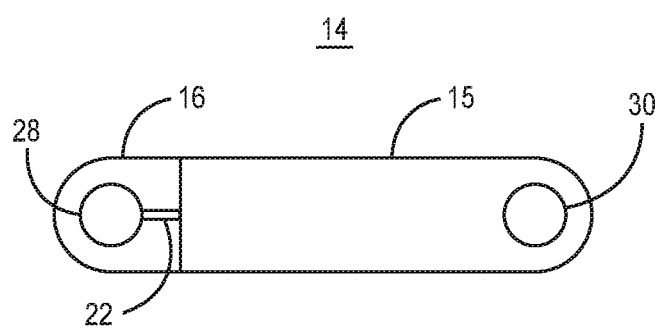
FIG. 2 is a diagram of the fluid status monitor of FIG. 1.

FIG. 1 is a conceptual diagram of a patient monitoring system 10 including an implantable fluid status monitor (FSM) 14 implanted in a patient 12 and an external device 40 configured to communicate wirelessly with FSM 14. FIG. 2 is a diagram of FSM 14. FSM 14 includes a housing 15 that forms a hermetic seal that protects internal components of FSM 14. Internal components include circuitry for cardiac electrical signal sensing, generating a drive current signal and recording a resulting voltage signal, and generating a fluid status signal. The housing 15 may be formed of a conductive material, such as titanium or titanium alloy. A portion of housing 15 may function as an electrode 30. In some examples, the housing 15 may include a plurality of electrodes on an outer portion of the housing. For example, portions of housing 15 that do not function as an electrode may be coated with an insulating material such as parylene or polyether etherketone (PEEK) and portions of housing 15 serving as an electrode 30 may be left uncoated. In other examples, one or more electrodes may be surface mounted on housing 15.

An electrode header 16 may be coupled to housing 15 having a surface-mounted electrode 28 that is electrically insulated from electrode 30 formed as a portion of housing 15. Header 16 may be formed from an electrically-insulating material, e.g., molded polyurethane or silicone material that is sealed to housing 15. Header 16 may include a cavity or recess for retaining electrode 28, leaving the surface of electrode 28 exposed. An insulated electrical conductor 22 extends through header 16 and electrically couples electrode 28 to internal electrical components of FSM 14 via an electrical feedthrough that extends into housing 15. Electrodes 28 and 30 may define a sensing electrode vector for receiving a cardiac electrical signal produced by heart 8. Electrodes 28 and 30 (and other electrodes described herein and shown in the accompanying drawings) may be, without limitation, titanium, platinum, iridium or alloys thereof and may include a low polarizing coating, such as titanium nitride, iridium oxide, ruthenium oxide, platinum black among others.

Electrodes 28 and 30 may be coupled to impedance sensing circuitry enclosed by housing 15 and used to inject a drive current signal into body tissue for determining an impedance measurement. Electrodes 28 and 30 may be used as voltage recording electrodes for recording the potential developed across electrodes 28 and 30 in response to the drive current signal. The recorded voltage is proportional to the tissue impedance and therefore correlated the content of fluid in the surrounding tissue. The voltage signal may be used directly as an impedance measurement or the impedance may be computed from the measured voltage and the known drive signal current amplitude. As such, electrodes 28 and 30 may function as a cardiac electrical signal sensing vector, drive signal electrodes, and the recording electrodes for measuring a voltage response to the impedance drive signal. In other examples, FSM 14 may include one or more electrodes on header 16 and one or more electrodes on housing 15 for a total of three or more electrodes. One pair of electrodes may be used for delivering a drive signal, and the same or a different pair of electrodes may be used to measure the resulting voltage signal. A third pair of electrodes, which may be the same or different than the drive signal electrode pair and/or the voltage recording electrode pair, may be used for sensing the cardiac electrical signal produced by heart 8.

An external device 40 is shown in FIG. 1 in telemetric communication with FSM 14 by a communication link 42. External device 40 may include a processor 52, memory 53, display unit 54, user interface 56 and telemetry unit 58. Processor 52 controls external device operations and processes data and signals received from FSM 14. Display unit 54, which may include a graphical user interface, displays data, programmable selections and settings and other information to a user for reviewing FSM operation, programming operating parameters and modes, and reviewing fluid status data retrieved from FSM 14. For example, processor 52 may generate a display on display unit 54 of the fluid status data, which may be in the form of a fluid status signal comprising data points including a combination of impedance metric(s) and/or calibrated cardiac signal amplitudes plotted at spaced apart time points as further described in conjunction with FIG. 8.

User interface 56 may include a mouse, touch screen, key pad or the like to enable a user to interact with external device 40 to initiate a telemetry session with FSM 14 for retrieving fluid status data from and/or transmitting data to FSM 14. Telemetry unit 58 includes a transceiver and antenna configured for bidirectional communication with a telemetry circuit included in FSM 14 and is configured to operate in conjunction with processor 52 for sending and receiving data relating to FSM functions via communication link 42. Communication link 42 may be established between FSM 14 and external device 40 using a radio frequency (RF) link such as BLUETOOTH®, Wi-Fi, or Medical Implant Communication Service (MICS) or other RF or selected communication frequency bandwidth.

External device 40 may be embodied as a home monitor or handheld device for interrogating FSM 14, to retrieve the fluid status data accumulated by FSM 14. In some examples, external device 40 may automatically interrogate FSM 14 to retrieve fluid status data on a scheduled, periodic basis, e.g., hourly, daily, or weekly. Additionally, or alternatively, external device 40 may be manually triggered to interrogate and retrieve data from FSM 14 and/or transmit commands or operating control parameters to FSM 14. In some examples, external device 40 may be coupled to a communication system (e.g., a cellular network) for transmitting data to a centralized clinical data base 50, a physician's computer or other centralized patient care system to provide remote monitoring of patient 12. External device 40 may be a MYCARELINK™ Patient Monitor available from Medtronic, Inc. Minneapolis Minn., USA, in one example. External device 40 may be a dedicated monitoring device or may be a smartphone, tablet or personal computer running a patient monitoring application.

A clinician may access the patient's fluid status data from clinical data base 50 to review the patient's fluid status condition for managing the patient's clinician condition and therapy. A clinician may manually access data from clinical data base 50. The clinician may be notified by an alert when new fluid status data from a patient is available and/or when a change in the fluid status signal generated by FSM 14 may be indicative of a potentially serious condition that warrants medical attention, e.g., relating to hypervolemia or hypovolemia. FSM 14 or external device 40 may generate an alert to notify the patient 12 and/or a clinician via external device 40 and centralized data base 50.

In other examples, external device 40 may be embodied as a programmer used in a hospital, clinic or physician's office to retrieve data from FSM 14 and to program operating parameters and algorithms in FSM 14 for controlling fluid status monitoring and other functions. Control parameters used to acquire fluid status data and generate fluid status signals according to the techniques disclosed herein may be programmed into FSM 14 using external device 40. Aspects disclosed herein attributed to external device 40 may be implemented in a CARELINK® Programmer, e.g., as described in the MEDTRONIC CARELINK® Model 2090 Programmer Reference Manual, MEDTRONIC, Inc. Minneapolis Minn., USA, 2013, incorporated herein by reference in its entirety.

Figure 3:
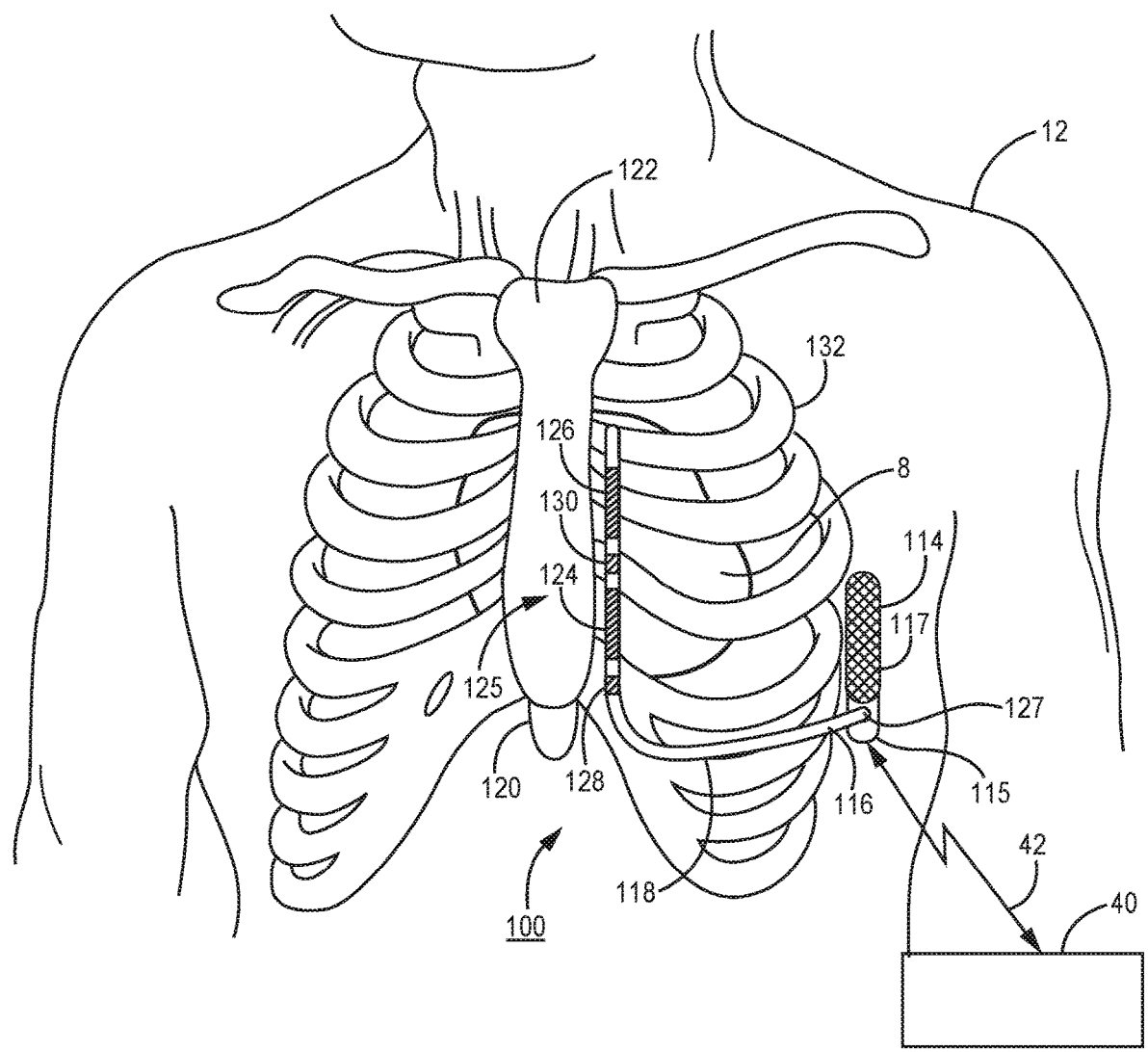
FIG. 3 is a conceptual diagram of a fluid status monitoring system according to another example.

FIG. 3 is a conceptual diagram of a FSM system 100 according to another example. FSM 14 of FIGS. 1 and 2 may be a monitoring only device without therapy delivery capabilities. In other examples, fluid status monitoring techniques disclosed herein may be implemented in a pacemaker, implantable cardioverter defibrillator (ICD), drug delivery pump, neurostimulator or other medical device that is capable of delivering a therapy in addition to monitoring the patient's fluid status (and optionally other physiological signals such as cardiac signals, patient activity, pressure signals, etc.). In FIG. 3, the FSM system 100 is shown including an ICD 114 coupled to an extra-cardiovascular lead 116. An "extra-cardiovascular lead" as used herein, refers to a lead that is implanted outside the heart and blood vessels of the patient's cardiovascular system. An extra-cardiovascular lead may extend subcutaneously, sub-muscularly or intra-thoracically, for example. ICD 114 is shown in wireless communication with external device 40, which may be used to retrieve data acquired by ICD 114 and transmit programming commands to ICD 114 as generally described above in conjunction with FIG. 1.

ICD 114 includes a housing 115 that forms a hermetic seal that protects internal components of ICD 114. As will be described in further detail herein, housing 115 may house one or more processors, memories, transceivers, sensors, cardiac electrical signal sensing circuitry, power sources and other components for sensing cardiac electrical signals, making impedance measurements and generating a fluid status signal. Internal components may further include pulse generating circuitry and one or more processors for detecting a heart rhythm and controlling the pulse generating circuitry to deliver electrical stimulation pulses to treat an abnormal heart rhythm. The housing 115 of ICD 114 may be formed of a conductive material, such as titanium or titanium alloy. The housing 115 may function as a housing electrode (sometimes referred to as a can electrode). Housing 115 may be used in conjunction with one or more electrodes carried by lead 116 for sensing cardiac electrical signals and in measuring impedance. Housing 115 may be used as an active can electrode for use in delivering cardioversion/defibrillation (CV/DF) shocks or other high voltage pulses, including cardiac pacing pulses. In other examples, housing 115 may be available for use in delivering unipolar, cardiac pacing pulses in conjunction with a lead-based cathode electrode. In other instances, the housing 115 of ICD 114 may include a plurality of electrodes on an outer portion of the housing. In some examples, one or more electrodes are provided on the outer portion of the housing 115 for acquiring amplitudes of a subcutaneous (or submuscular) ECG signal that can be calibrated to correlate to an impedance signal and the patient's fluid status. The outer portion(s) of the housing 115 functioning as an electrode(s) may be coated with a material, such as titanium nitride to reduce post-stimulation polarization artifact.

ICD 114 includes a connector assembly 117 (also referred to as a connector block or header) that includes electrical feedthroughs crossing housing 115 to provide electrical connections between conductors extending within the lead body 118 of lead 116 and electronic components included within the housing 115 of ICD 114. Lead 116 includes an elongated lead body 118 having a proximal end 127 that includes a lead connector (not shown) configured to be connected to ICD connector assembly 117 and a distal portion 125 that includes one or more electrodes. In the example illustrated in FIG. 3, the distal portion 125 of lead 116 includes defibrillation electrodes 124 and 126 and pace/sense electrodes 128 and 130. Electrodes 124 and 126 (and in some examples housing 115) are referred to herein as defibrillation electrodes because they are utilized, individually or collectively, for delivering high voltage stimulation therapy (e.g., cardioversion or defibrillation shocks). Electrodes 124 and 126 may be elongated coil electrodes and generally have a relatively high surface area for delivering high voltage shock therapy pulses compared to the surface area of the pacing and sensing electrodes 128 and 130, which may be used to deliver cardiac pacing pulses that are lower in pulse energy than CV/DF shock pulses. However, electrodes 124 and 126 and housing 115 may also be utilized to provide pacing functionality, sensing functionality or both pacing and sensing functionality in addition to or instead of high voltage CV/DF shock therapy. In this sense, the use of the term "defibrillation electrode" herein should not be considered as limiting the electrodes 124 and 126 for use in only CV/DF shock therapy applications. Electrodes 124 and 126 may be used in a pacing electrode vector for delivering extra-cardiovascular pacing pulses. Electrodes 124 and 126 may be used in a sensing vector used to sense a cardiac electrical signal for monitoring the patient's fluid status and for detecting abnormal heart rhythms, such as ventricular tachycardia (VT) and ventricular fibrillation (VF).

Electrodes 128 and 130 are relatively smaller surface area electrodes for delivering relatively lower voltage pacing pulses and for sensing cardiac electrical signals and monitoring the patient's fluid status. Electrodes 128 and 130 are referred to herein as pace/sense electrodes because they are generally configured for use in relatively lower voltage applications than defibrillation electrodes 124 and 126. Electrodes 128 and 130 may be used as either a cathode or anode for delivery of pacing pulses, and/or sensing of cardiac electrical signals. In some instances, electrodes 128 and 130 may provide only pacing functionality, only sensing functionality or both.

In the example illustrated in FIG. 3, electrode 128 is located proximal to defibrillation electrode 124, and electrode 130 is located between defibrillation electrodes 124 and 126. In other examples, electrodes 128 and 130 may be positioned at other locations along lead 116, which may include one or more pace/sense electrodes. Electrodes 128 and 130 are illustrated as ring electrodes; however electrodes 128 and 130 may comprise any of a number of different types of electrodes, including ring electrodes, short coil electrodes, hemispherical electrodes, directional electrodes, or the like.

Lead 116 extends subcutaneously or submuscularly over the ribcage 132 medially from the connector assembly 117 of ICD 114 toward a center of the torso of patient 12, e.g., toward xiphoid process 120 of patient 12. At a location near xiphoid process 120, lead 116 bends or turns and extends superiorly over ribcage 132, substantially parallel to sternum 122. Alternatively, the distal portion 125 of lead 116 may extend beneath ribcage 132 and sternum 122, e.g., within the anterior mediastinum in a substernal position. In one example, the distal portion 125 of lead 116 extends along the posterior side of sternum 122 substantially within the loose connective tissue and/or substernal musculature of anterior mediastinum 136. A lead implanted such that the distal portion 125 is substantially within anterior mediastinum 136 may be referred to as a "substernal lead."

In the example illustrated in FIG. 3, lead 116 is located substantially parallel to sternum 122. In other instances, however, lead 116 may be implanted such that it is centered under (in a substernal position) or centered over sternum 122 or be offset laterally from the center of sternum 122. In some instances, lead 116 may angle laterally away from sternum 122 such that distal portion 125 of lead 116 extends over (or within) the ribcage 32 in addition to or instead of over (or beneath) sternum 122. In other examples, the distal portion 125 of lead 116 may be implanted in other extra-cardiovascular, intra-thoracic locations, including the pleural cavity or around the perimeter of and adjacent to the pericardium of heart 8. Alternatively, lead 16 may be placed along other subcutaneous or submuscular paths. The path of lead 16 may depend on the location of ICD 114, the arrangement and position of electrodes carried by the lead distal portion 25, and/or other factors. Other implant locations and lead and electrode arrangements that may be used in conjunction with the fluid status monitoring techniques described herein are generally disclosed in U.S. Pat. Application Publication No. 2015/0306375 (Marshall, et al.) and U.S. Pat. No. 9,855,414 (Marshall, et al.), both of which are incorporated herein by reference in their entirety.

Lead body 118 may be a flexible lead body without preformed curves or bends. In other examples an extra-cardiovascular lead including one or more defibrillation electrodes and/or one or more pacing and sensing electrodes may be carried by a lead body having one or more preformed curves or bends or a serpentine, undulating or zig-zagging distal portion of the lead body 118. Examples of other extra-cardiovascular leads that may be implemented with the techniques described herein are generally disclosed in U.S. Pat. Application Publication No. 2016/0158567 (Marshall, et al.), incorporated herein by reference in its entirety. The techniques disclosed herein are not limited to a particular electrode arrangement or lead body design, however.

Electrical conductors (not illustrated) extend through one or more lumens of the elongated lead body 118 of lead 116 from the lead proximal end 127 to each of electrodes 124, 126, 128, and 130 located along the distal portion 125 of the lead body 118. The conductors electrically couple the electrodes 124, 126, 128, and 130 to circuitry, such as a therapy delivery circuit and/or a sensing circuit, of ICD 114 via connections in the connector assembly 117, including associated electrical feedthroughs crossing housing 115. The electrical conductors transmit therapy from a therapy circuit within ICD 114 to one or more of defibrillation electrodes 124 and 126 and/or pace/sense electrodes 128 and 130 and transmit cardiac electrical signals produced by the patient's heart 8 from one or more of defibrillation electrodes 124 and 126 and/or pace/sense electrodes 128 and 130 to the sensing circuit within ICD 114.

ICD 114 may obtain a cardiac electrical signal corresponding to electrical activity of heart 8 via a sensing electrode vector selected from electrodes 124, 126, 128 and 130 and housing 115. In some examples, housing 115 of ICD 114 is used in combination with one or both of electrodes 128 in a sensing electrode vector. ICD 114 may even receive a cardiac electrical signal using a sensing vector that includes one or both defibrillation electrodes 124 and/or 126, e.g., between electrodes 124 and 126 or between one of electrodes 124 or 126 in combination with one of electrodes 128, 130 and/or housing 15.

ICD 114 analyzes the cardiac electrical signals received from one or more of sensing vectors to monitor for abnormal rhythms, such as bradycardia or tachycardia. ICD 114 may analyze the heart rate and/or morphology of the cardiac electrical signals to monitor for tachyarrhythmia in accordance with any of a number of tachyarrhythmia detection techniques. ICD 114 generates and delivers electrical stimulation therapy in response to detecting an abnormal heart rhythm. ICD 114 may deliver anti-tachycardia pacing (ATP) in response to tachycardia detection and in some cases may deliver ATP prior to a CV/DF shock or during high voltage capacitor charging in an attempt to avert the need for delivering a CV/DF shock. ATP may be delivered using an extra-cardiovascular pacing electrode vector selected from any of electrodes 124, 126, 128, 130 and/or housing 115.

If ATP is not delivered or does not successfully terminate the tachycardia or when ventricular fibrillation is detected, ICD 114 may deliver one or more CV/DF shocks via one or both of defibrillation electrodes 124 and 126 and/or housing 115. ICD 114 may deliver the CV/DF shocks using electrodes 124 and 126 individually or together as a cathode (or anode) and with the housing 115 as an anode (or cathode).

ICD 114 may be configured as a FSM having components configured to determine impedance, including circuitry for generating an impedance drive signal applied to a selected drive electrode pair and sensing circuitry for measuring the voltage across a recording electrode pair. The drive electrode pair and the recording electrode pair may be the same or different electrode pairs selected from any of the available electrodes 124, 126, 128, 130 and housing 115. ICD 114 may additionally monitor the amplitude of a cardiac electrical signal (produced by the patient's heart 8) for use in generating a fluid status signal in combination with impedance measurements. The cardiac electrical signals may be received by a sensing electrode vector selected from any of the available electrodes 124, 126, 128 and 130 and housing 115. In some cases, the sensing electrode vector used to acquire cardiac electrical signals from fluid status monitoring may be the same recording electrode pair used to obtain impedance measurements. The received cardiac signals are passed to a processor configured to determine cardiac signal amplitudes that may be calibrated relative to one or more impedance measurements and used to generate a fluid status signal.

Figure 4:
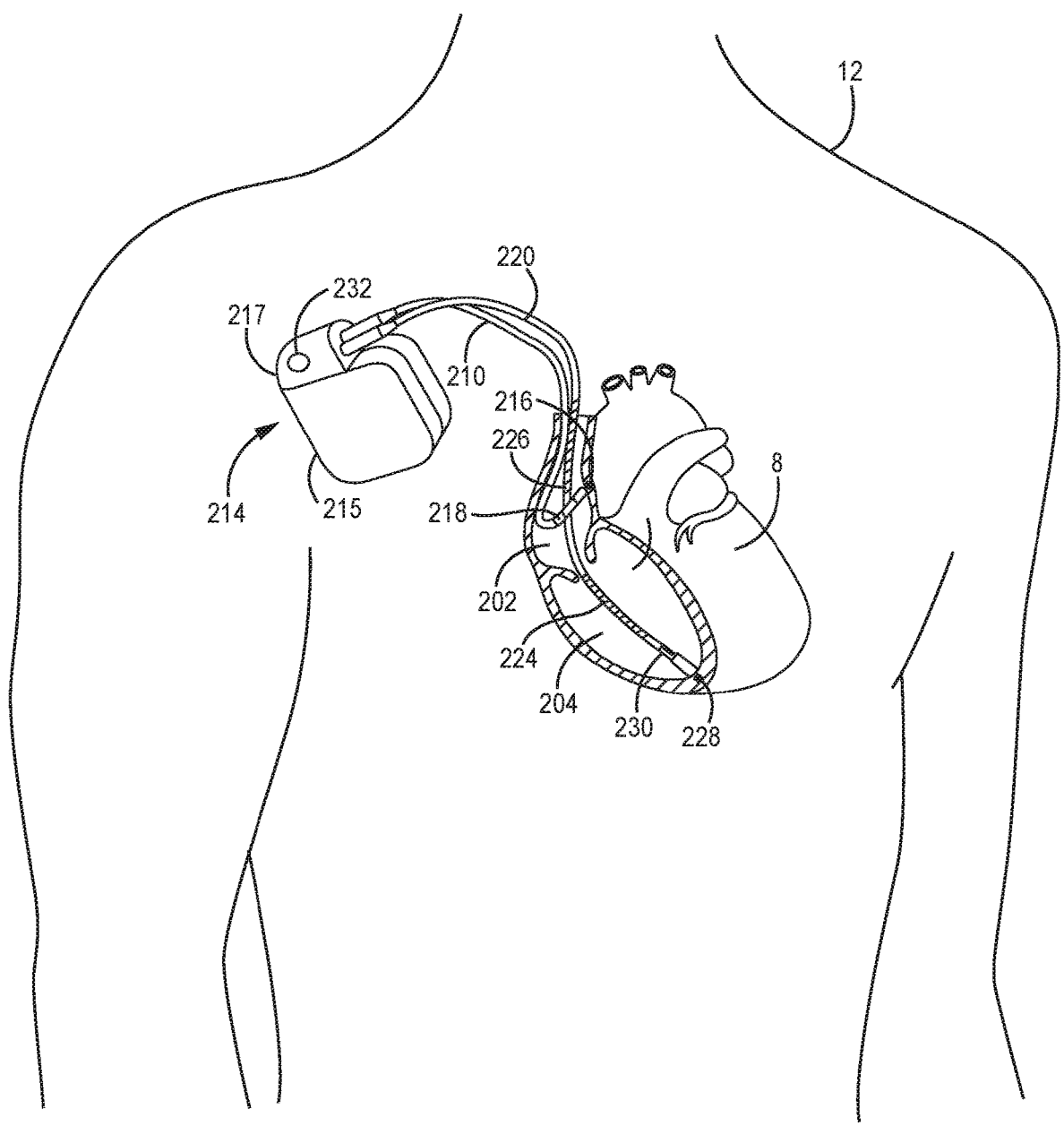
FIG. 4 is a conceptual diagram of a fluid status monitoring system according to another example.

FIG. 4 is a conceptual diagram of a medical device system 200 including a FSM embodied as an ICD 214 according to another example. ICD 214 may be coupled to a transvenous medical lead which is adapted for positioning electrodes within a heart chamber. While the system 100 of FIG. 3 is shown to include an extra-cardiovascular lead, it is to be understood that the fluid status monitoring techniques disclosed herein may be implemented in a medical device coupled to a transvenous lead, which may position one or more electrodes within the patient's heart 8. One example of a medical device system including one or more transvenous leads is generally described in U.S. Pat. No. 6,931,272 (Burnes), incorporated herein by reference in its entirety. Other fluid status monitoring systems may include an epicardial lead carrying one or more electrodes in contact with the pericardium or epicardial surface of the heart 8.

In the example of FIG. 4, ICD 214 is coupled to a transvenous lead carrying electrodes for sensing cardiac electrical signals and impedance signals and may be used for delivering electrical stimulation therapy, e.g., bradycardia pacing, ATP, cardiac resynchronization therapy (CRT) and/ or CV/DF shocks. ICD 214 is shown implanted in a right pectoral position in FIG. 4; however it is recognized that ICD 214 may be implanted in a left pectoral position, particularly when ICD 214 includes cardioversion and defibrillation capabilities using housing 215 as an electrode.

ICD 214 is illustrated as a dual chamber device for sensing and therapy delivery in an atrial chamber 202 and a ventricular chamber 204 of heart 8. As such, ICD 214 includes connector assembly 217 having two connector bores for receiving proximal connectors of a right atrial (RA) lead 210 and a right ventricular (RV) lead 220. In other examples ICD 214 may be a single chamber device, e.g., connectable only to RA lead 210 or to RV lead 220, or ICD 214 may be a multi-chamber device including a third connector bore, e.g., for receiving a coronary sinus lead to enable ICD 214 to sense left ventricular signals and deliver electrical stimulation pulses to the left ventricle. For example, ICD 214 may be coupled to a multi-polar coronary sinus lead as generally disclosed in U.S. Pat. No. 9,278,220 (Ghosh, et al.), incorporated herein by reference in its entirety. In some examples, electrodes carried by a coronary sinus lead, e.g., a quadripolar coronary sinus lead, may be used in acquiring fluid status signal data according to the techniques disclosed herein.

RA lead 210 may carry a distal tip electrode 216 and ring electrode 218 spaced proximal from the tip electrode 216 for delivering pacing pulses to the right atrium 202 and obtaining atrial electrical signals for producing an atrial intracardiac electrogram (EGM) signal by ICD 214. RV lead 220 may carry pacing and sensing electrodes 228 and 230 for delivering RV pacing pulses to the right ventricle 204 and obtaining ventricular electrical signals for producing an RV EGM signal by ICD 214. RV lead 220 may also carry RV defibrillation electrode 224 and a superior vena cava (SVC) defibrillation electrode 226. Defibrillation electrodes 224 and 226 are shown as coil electrodes spaced apart proximally from the distal pacing and sensing electrodes 228 and 230.

Housing 215 encloses circuitry, as further described below, configured to detect arrhythmias and provide electrical stimulation therapy as needed using the electrodes 216, 218, 224, 226, 228 and 230 of transvenous leads 210 and 220. Housing 215 may function as an electrode for use in unipolar cardiac electrical signal sensing. In some examples, housing 215 may include two or more electrodes formed along the outer surface of housing 215 and/or header 217, e.g., electrode 232, to provide a pair of subcutaneous tissue impedance sensing electrodes that may also be used for acquiring a subcutaneous (or submuscular) ECG signal.

According to the techniques described herein, ICD 214 may operate as a FSM by sensing cardiac electrical signals, determining amplitudes of the cardiac electrical signal, e.g., R-wave amplitudes or P-wave amplitudes, and adjusting the cardiac electrical signal amplitudes according to an impedance-based calibration relationship. The cardiac signal amplitudes are correlated to tissue impedance and are used to generate a fluid status signal. The cardiac signal amplitudes may be calibrated according to tissue impedance measurements made by ICD 214 using housing 215 as an electrode in combination with any of the lead-based electrodes 216, 218, 224, 226, 228 or 230. ICD 214 may generate a fluid status signal using a combination of tissue impedance measurements and calibrated cardiac signal amplitudes.

In various examples, a cardiac electrical signal sensed for fluid status monitoring may be sensed using a bipolar sensing vector selected between a pair of endocardial electrodes carried by leads 210 or 220, a unipolar sensing vector between housing 215 and an endocardial electrode carried by one of leads 210 or 220, or a subcutaneous electrode pair including housing 215 and header electrode 232. Because of the potential delays and differences in distribution of fluid in the various compartments of the body (e.g., intravascular, interstitial, and intracellular), different electrode combinations selected for monitoring fluid status may be exposed to different compartmental impedance. For example, an impedance signal or a cardiac electrical signal sensed using a bipolar electrode pair within heart 8 may be less sensitive to fluid changes occurring in extravascular compartments. An impedance signal or cardiac electrical signal sensed using a unipolar electrode pair between the housing 215 and a lead-based electrode positioned within the heart may reflect a combination of multiple compartment fluid statuses, including intravascular and extravascular fluid compartments, between the two electrodes.

A subcutaneous ECG signal acquired by ICD 214 (or FSM 14 of FIG. 1 or ICD 114 of FIG. 3), e.g., using housing-based electrodes, may be sensitive to fluid changes that are cross-compartmental, because the ECG signal amplitude may be correlated to the impedance of the intervening compartments between the heart and the subcutaneous electrodes. A local subcutaneous impedance measurement obtained using subcutaneous electrodes, however, will reflect local impedance changes and may be less sensitive to fluid changes within the heart itself or in the intervening tissue between the heart and the subcutaneous electrodes.

When different combinations of one or more body fluid compartments contribute to the impedance signal and the cardiac electrical signal acquired for fluid status monitoring, each signal may reflect different impedances and/or delays in impedance changes due to the fluid status of the different combinations of body fluid compartments. These differences may be accounted for by the fluid status monitoring algorithm disclosed herein. For example, differences in impedance between combinations of body fluid compartments contributing to the cardiac electrical signal and the impedance signal may be accounted for by determining and updating a calibration relationship between cardiac signal amplitude and the impedance signal. Delays in changes in fluid status between different body fluid compartments contributing to each of the cardiac electrical signal and the impedance signal may be accounted for by time averaging the cardiac signal amplitude and/or impedance signal amplitudes over appropriate time intervals.

ICD 214 may be capable of bidirectional wireless communication with an external device 40 (shown in FIG. 1) for retrieving fluid status data from ICD 214 and for programming fluid status monitoring control parameters and algorithms, as described above in conjunction with FIG. 1, as well as cardiac signal sensing and therapy delivery control parameters.

Figure 5:
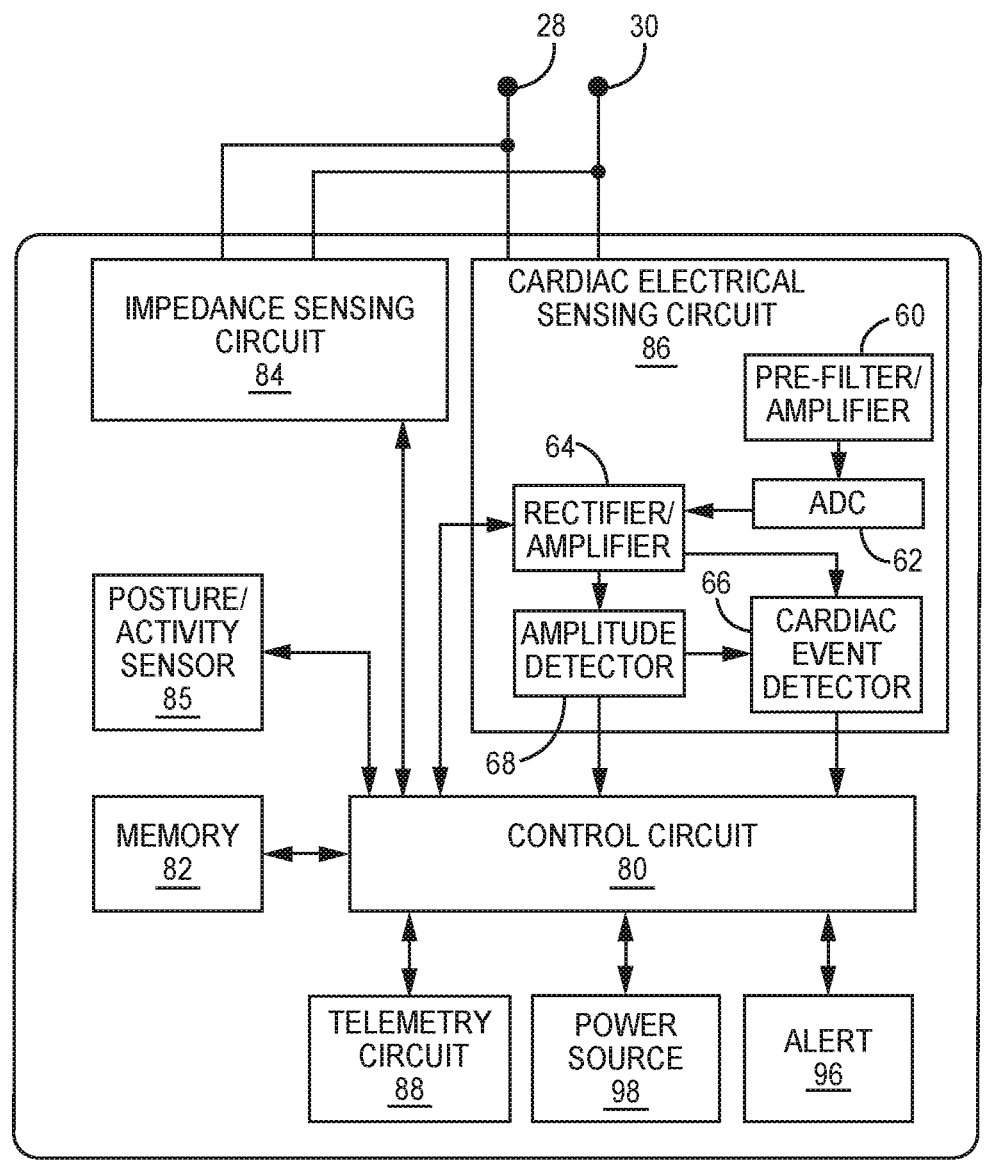
FIG. 5 is a functional block diagram of a fluid status monitor according to one example.

FIG. 5 is a block diagram of FSM 14 of FIG. 1 according to one example. While reference is made primarily to FSM 14, which may be a monitoring only device without therapy delivery capabilities, the circuitry included in FSM 14 and the functionality attributed to the circuitry and components of FSM 14 may be included in any of the other examples of medical devices listed or described above, including ICD 114 (FIG. 3) and ICD 214 (FIG. 4), which may include additional components as described below for providing cardiac electrical stimulation therapies.

FSM 14 includes a control circuit 80, memory 82, an impedance sensing circuit 84, cardiac electrical sensing circuit 86, telemetry circuit 88, and power source 98. In some examples, FSM 14 may include a posture and activity sensor 85 and/or a patient alert generator 96. Power source 98 provides power to the circuitry of FSM 14, including each of the circuits 80, 82, 84, 85, 86, 88 and 96 as needed. Power source 98 may include one or more energy storage devices, such as one or more rechargeable or non-rechargeable batteries.

The functional blocks shown in FIG. 5 represent one or more discrete and/or integrated electronic circuit components capable of producing the fluid status monitoring functions attributed to FSM 14 herein and may be embodied as one or more processors, hardware, firmware, software, or any combination thereof. Depiction of different features as circuit blocks is intended to highlight different functional aspects and does not necessarily imply that such blocks must be realized by separate hardware, firmware or software components. Rather, functionality associated with one or more circuits may be performed by separate or integrated hardware, firmware and/or software components.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 or other sensing device circuits to perform various functions attributed to FSM 14. The non-transitory computer readable media storing the instructions may include any of the media listed above.

Cardiac electrical signal sensing circuit 86, also referred to herein as "sensing circuit" 86, is coupled to a sensing electrode vector in order to acquire a cardiac electrical signal, which may include P-waves attendant to the depolarization of the atrial myocardium, R-waves (and the QRS complex) attendant to the depolarization of the ventricular myocardium and T-waves attendant to repolarization of the ventricular myocardium. Sensing circuit 86 is coupled to electrodes 28 and 30 in the example of FSM 14 of FIG. 1. It is to be understood that sensing circuit 86 may be coupled to any or all available electrodes coupled to a medical device configured to perform the fluid status monitoring techniques disclosed herein. For example, in the case of ICD 114, sensing circuit 86 may be coupled to each of electrodes 124, 126, 128 and 130 and housing 115 and may include switching circuitry for selecting a sensing electrode vector from the available electrodes. Switching circuitry may include a switch array, switch matrix, multiplexer, or any other type of switching device suitable to selectively couple selected electrodes to an input filter of sensing circuit 86. In examples that include more than one sensing electrode vector, sensing circuit 86 may be a multi-channel sensing circuit configured to receive and monitor more than one cardiac electrical signal.

Sensing circuit 86 may include one or more filters, amplifiers, analog-to-digital converters, rectifiers, sense amplifiers, comparators or other threshold detectors, peak detectors or other analog or digital components. The components of sensing circuit 86 may be configured to generate a multi-bit digital ECG signal and may sense cardiac events, e.g., P-waves and/or R-waves. For example, sensing circuit 86 may receive a cardiac electrical signal via electrodes 28 and 30 by a pre-filter and amplifier circuit 60. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. The pre-filter and amplifier circuit 60 may further include an amplifier to amplify the "raw" cardiac electrical signal passed to an analog-to-digital converter (ADC) 62. Sensing circuit 86 may include a rectifier 64 to produce a rectified, amplified, digital signal that may be passed to control circuit 80, to a cardiac event detector 66 and/or to an amplitude detector 68.

Cardiac event detector 66 may include a sense amplifier, comparator or other cardiac event detection circuitry for sensing a cardiac event, e.g., an R-wave or P-wave, in response to a cardiac event threshold amplitude crossing by the cardiac electrical signal (outside any applied blanking periods). The threshold amplitude may be an auto-adjusting threshold. For example, cardiac event detector 66 may include a sense amplifier or other detection circuitry that compares the incoming rectified, cardiac electrical signal to an R-wave detection threshold, which may be an auto-adjusting threshold. When the incoming signal crosses the R-wave detection threshold, the cardiac event detector 66 produces an R-wave sensed event signal (R-sense) that may be passed to control circuit 80. Control circuit 80 may use cardiac sensed event signals for monitoring the patient's heart rhythm.

Rectifier/amplifier 64 may pass the digitized, rectified cardiac electrical signal to amplitude detector 68. Amplitude detector 68 determines fiducial amplitude values of the cardiac electrical signal for monitoring the patient's fluid status. Amplitude detector 68 may be a peak detector that identifies the maximum peak amplitude during a cardiac cycle, e.g., the maximum peak amplitude of the R-wave of the rectified signal or a peak-to-peak amplitude of the non-rectified signal. The sensed event signals produced by cardiac event detector 66 may be passed to amplitude detector 68 for starting a maximum peak amplitude search. In other examples, the cardiac event signal may be used as reference time point relative to which amplitude detector 68 determines a cardiac signal amplitude for use in monitoring the patient's fluid status.

Amplitude detector 68 may pass a determined cardiac signal amplitude to control circuit 80 (e.g., as a multi-bit digital signal). Control circuit 80 may use the received cardiac signal amplitudes for generating a fluid status signal as described in greater detail below. In other examples, control circuit 80 may receive the digitized cardiac electrical signal directly from rectifier/amplifier 64 (or ADC 62). A signal processor included in control circuit 80 may determine the cardiac electrical signal amplitudes needed for generating a fluid status signal directly from the cardiac electrical signal.

The R-wave maximum peak amplitude and/or other cardiac signal amplitudes received from sensing circuit 86 or determined by control circuit 80 from the digitized cardiac electrical signal received from sensing circuit 86 may be used in monitoring fluid status. For example, P-wave amplitude and/or the T-wave amplitude may be used in generating fluid status signal points in addition to or alternatively to the R-wave peak amplitude. While the illustrative examples described herein refer to cardiac electrical signal amplitude and an amplitude detector 68 is shown in FSM 14, it is contemplated that other features of the cardiac electrical signal correlated to amplitude and to impedance may be determined from the cardiac electrical signal for monitoring fluid status. For example, the integral of the QRS signal or the integral of the QRST segment may be determined as generally disclosed in the above-incorporated '272 patent (Burnes).

Changes in the amplitude of the cardiac electrical signal, and therefore an integral of the cardiac electrical signal, are correlated to changes in impedance due to changes in intravascular and extravascular fluid volume. An increase in fluid, associated with fluid retention which may lead to edema, decreases impedance resulting in a decrease in the cardiac electrical signal amplitude. Conversely, a decrease in fluid, e.g., associated with diuresis which may lead to dehydration, increases impedance resulting in an increase in cardiac electrical signal amplitude. Control circuit 80 is configured to generate fluid status signal points from the received cardiac electrical signal amplitude detector 68 and compare the fluid status signal amplitude points (or a trend or slope thereof) to one or more thresholds or ranges for detecting a change in the patient's fluid status.

A change in fluid status that may be detected by control circuit 80 may be an increased fluid status, indicating fluid retention in the tissue volume between the electrodes 28 and 30 and the heart as the current source. The changes in fluid status detected by control circuit 80 may include a decreased fluid status, indicating over-diuresis or dehydration or progression of anemia. Control circuit 80 may be configured to detect a normal fluid status (which may be tailored to the patient) when the generated fluid status signal points remain within a predetermined range defined by a minimum threshold and a maximum threshold. Increased and decreased fluid status may be detected when the fluid status signal points fall outside (above or below) the predetermined range for at least a predetermined time interval or predetermined frequency within a given time period (e.g., within one hour, twelve hours, one day, one week, etc.). Detection of an increased or decreased fluid status may be responded to by generating a patient or physician alert and/or by delivering or adjusting an automatic therapy delivered by the FSM (when capable of automatic therapies such as ICD 114 or ICD 214) or another medical device, which may be an implantable or external drug pump, ICD, or pacemaker as examples.

FSM 14 includes an impedance sensing circuit 84 that is controlled by control circuit 80 to generate a current signal that is applied to electrodes 28 and 30 as a non-therapeutic drive signal. The resultant voltage signal developed across electrodes 28 and 30 may be passed to control circuit 80 as an impedance signal. In other examples, control circuit 80 may receive the voltage signal from impedance sensing circuit 84 and convert the voltage signal to an actual impedance signal based on the known drive current signal. Control circuit 80 may determine multiple impedance metrics from the impedance signal and multiple, contemporaneous cardiac electrical signal amplitudes from the cardiac electrical signal. Control circuit 80 determines a calibration relationship between the impedance metrics and the cardiac electrical signal amplitudes. In some examples, determining the calibration relationship may include determining a calibration formula that may be stored in memory 82. Control circuit 80 uses the calibration formula to convert cardiac electrical signal amplitudes to fluid status signal points to generate the fluid status signal. In other examples, determining the calibration relationship may include generating a look-up table of calibrated cardiac electrical signal amplitudes. The calibration relationship may be stored as a look-up table in memory 82 instead of parameters defining a calibration formula that requires additional computations each time a cardiac electrical signal amplitude is determined during fluid status monitoring. Upon determining a cardiac electrical signal amplitude during fluid status monitoring, control circuit 80 may look up the calibrated cardiac electrical signal amplitude corresponding to the determined cardiac electrical signal amplitude.

Control circuit 80 may compare the fluid status signal to one or more thresholds or ranges for detecting a fluid status condition. In some examples, the fluid status signal incorporates both impedance metrics determined from the impedance signal and calibrated cardiac electrical signal points, which may be interpolated at time points between impedance metrics. In other examples, the fluid status signal includes only the calibrated cardiac electrical signal points, and the impedance measurements are determined only for determining the calibration relationship applied to the cardiac electrical signal amplitudes. The calibration relationship may be periodically updated using the impedance measurements.

FSM 14 may include a posture and activity sensor 85. Posture sensor 85 may be a multi-axis accelerometer, e.g., a three-dimensional accelerometer having three accelerometer elements arranged orthogonally in x-, y-, and z-axes. Each axis of the posture and activity sensor 85 may be defined by a piezoelectric element, micro-electrical mechanical system (MEMS) device or other sensor element capable of producing an electrical signal in response to changes in acceleration imparted on the sensor element, e.g., by converting the acceleration to a force or displacement that is converted to the electrical signal. The DC component of the signal produced by each accelerometer axis corresponds to gravitational force exerted along that axis or vector. As such, the DC component of each axis may be used for determining the patient's posture. A posture sensor that may be used in a FSM is generally disclosed in U.S. Pat. No. 6,044,297 (Sheldon, et al.), incorporated herein by reference in its entirety.

The output of one or more axes of posture sensor 85 may be passed to control circuit 80 for discriminating between patient postures for use in monitoring the patient's fluid status. Intra- and extra-vascular compartmental fluid volumes may shift with changes in patient body posture. As such, changes in a fluid status signal generated by control circuit 80 may be due to changes in posture and may or may not reflect a clinically relevant change in fluid status but rather a shift in fluid distribution. Control circuit 80 may be configured to detect a change in the patient's posture and generate a fluid status signal using calibrated cardiac electrical signal amplitudes for two or more different patient postures. For example, one fluid status signal may be generated using cardiac electrical signal amplitudes when the posture sensor signal indicates a generally upright position (e.g., standing or sitting) and another fluid status signal may be generated using cardiac electrical signal amplitudes when the posture sensor signal indicates a generally non-upright position (e.g., a reclined or lying position). In other examples, multiple, more specific, body postures or categories of postures may be identified and detected from the posture sensor signal. Other body postures may include supine, prone, right-side lying and left-side lying as examples. Different calibration formulas or look-up tables of calibrated cardiac electrical signal amplitudes may be established for different body postures for determining fluid status signal points from cardiac electrical signal amplitudes acquired during the different, respective body postures. A fluid status signal may be generated for each respective body posture (or groupings of similar postures) or a single fluid status signal may be generated using the appropriately calibrated cardiac electrical signal amplitudes merged together over time.

In some examples, control circuit 80 is configured to monitor a trend in the fluid status signal after detecting a posture change. In this way, control circuit 80 may determine a time or slope of a fluid shift following a body posture change. In some conditions, the time for a shift of fluid volume may be disease related and may provide a clinician with useful diagnostic or prognostic information for managing patient therapy. The shift in fluid volume with postural change may be between body regions, e.g., from legs to torso, and/or between body compartments, e.g., between intravascular and interstitial compartments.

Patient alert circuit 96 may be controlled by control circuit 80 to generate an alert signal that is perceptible by the patient, e.g., an audible sound, buzzing or vibration. A patient alert may be generated by alert circuit 96 in response to detecting a fluid status change, e.g., greater than or less than a predetermined threshold or outside a predefined acceptable range. The patient may be instructed by his/her physician to respond to an alert, e.g., by contacting the physician, adjusting a prescribed medication or other action that may remediate the fluid status condition.

Telemetry circuit 88 includes a transceiver and antenna for communicating with another device, such as an external device 40 (FIG. 1). Under the control of control circuit 80, telemetry circuit 88 may receive downlink telemetry from and send uplink telemetry to external device 40 or another external device. Telemetry circuit 88 may be controlled to transmit fluid status data, which may be in the form of a fluid status signal generated using cardiac electrical signal amplitudes, to external device 40 for display to a user or further transmission via a communication system to a centralized patient data base or physician to enable remote monitoring of the patient. Telemetry circuit 88 may receive an interrogation command and programming commands from the external device 40 for use by control circuit 80 in controlling FSM functions.

Figure 6:
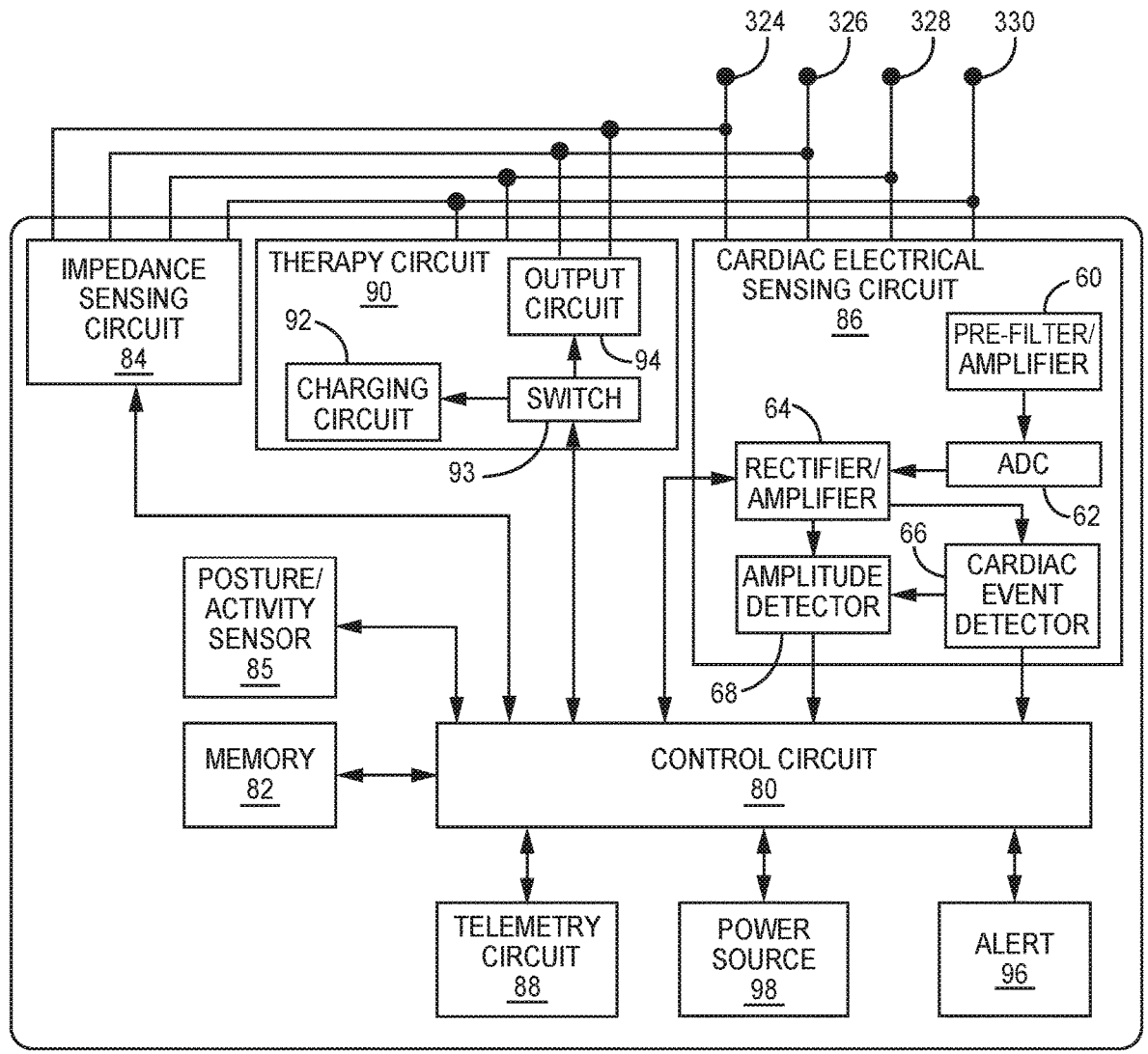
FIG. 6 is a functional block diagram of a fluid status monitor according to another example.

FIG. 6 is a block diagram of a FSM 314 according to another example. FSM 314 includes therapy delivery capabilities and may correspond to ICD 114 or ICD 214. FSM 314 includes the components described above in conjunction with FIG. 5, including control circuit 80, memory 82, impedance sensing circuit 84, cardiac electrical sensing circuit 86, posture sensor 85, telemetry circuit 88, power source 98 and alert 96 configured to operate cooperatively for monitoring a patient's fluid status according to the techniques disclosed herein. Additionally, FSM 314 includes a therapy circuit 90 configured to generate cardiac electrical stimulation pulses such as cardiac pacing pulses and/or cardioversion/defibrillation pulses. When FSM 314 is capable of delivering cardiac electrical stimulation therapies, control circuit 80 may use cardiac sensed event signals received from cardiac event detector 66 and/or a digitized cardiac electrical signal from cardiac electrical sensing circuit 86 for detecting abnormal heart rhythms and/or controlling the timing of electrical stimulation pulses delivered to the patient's heart.

Therapy circuit 90 generates electrical pacing pulses that are delivered to the patient's heart via a therapy delivery electrode vector selected from available electrodes 324, 326, 328 and 330 coupled to FSM 314. Therapy circuit 90 may include a charging circuit 92, switching circuit 93 and an output circuit 94. Charging circuit 92 may include a holding capacitor that may be charged to a pacing pulse amplitude by a multiple of the battery voltage signal of power source 98 under the control of a voltage regulator. The pacing pulse amplitude may be set based on a control signal from control circuit 80. Switching circuit 93 may control when the holding capacitor of charging circuit 92 is coupled to the output circuit 94 for delivering a cardiac electrical stimulation pulse. For example, switching circuit 93 may include a switch that is activated by a timing signal received from control circuit 80 upon expiration of pacing interval and kept closed for a programmed pacing pulse width to enable discharging of the holding capacitor of charging circuit 92. The holding capacitor, previously charged to the pacing pulse voltage amplitude, is discharged across the electrode vector via an output capacitor of output circuit 94 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in FSM 314 for charging a pacing capacitor to a predetermined pacing pulse amplitude under the control of control circuit 80 and delivering a pacing pulse.

Therapy circuit 90 may be capable of delivering high voltage therapies, e.g., cardioversion/defibrillation shock pulses. In this case, charging circuit 92 may include one or more high voltage capacitors. When a shockable rhythm is detected, such as ventricular fibrillation, the HV capacitor(s) is(are) charged to a shock voltage amplitude by the charging circuit 92 according to the programmed shock energy. The charging circuit 92 may include a transformer in a processor-controlled charging circuit that is controlled by control circuit 80 for charging the high voltage capacitor(s) to a voltage that is much higher than a that used for generating pacing pulses. Control circuit 80 applies a signal to trigger discharge of the high voltage capacitor(s) upon detecting a feedback signal from therapy circuit 90 that the high voltage capacitors have reached the shock voltage amplitude required to deliver the programmed shock energy. In this way, control circuit 80 controls operation of the therapy circuit 90 to deliver CV/DF shocks using defibrillation electrodes, e.g., electrodes 124 and 126 (FIG. 3) which may correspond to electrodes 324 and 326 in FIG. 6 and/or housing 115 of ICD 214.

Output circuit 94 may include a high voltage output circuit, e.g., in the form of an H-bridge including multiple switches that are controlled by signals from control circuit 80. The switches included in switch 93 used to couple one or more holding capacitors of charging circuit 92 to output circuit 94 and switches included in an H-bridge or other circuit 94 may be implemented as silicon-controlled rectifiers (SCRs), insulated-gate bipolar transistors (IGBTs), metal-oxide-semiconductor field-effect transistors (MOSFETs), and/or other switching circuit components or combinations thereof.

In some examples, control circuit 80 may detect a change in fluid status meeting therapy delivery criteria. Control circuit 80 may control therapy circuit 90 to generate cardiac electrical stimulation pulses to deliver an electrical stimulation therapy to the patient's heart (or a nerve) to remediate the fluid status change. For example, if increased fluid is detected based on a decreasing, calibrated cardiac electrical signal amplitude, a pacing therapy may be adjusted or delivered to increase cardiac output and/or improve synchrony between the heart chambers (e.g., by increasing pacing rate or delivering cardiac resynchronization therapy).

Figure 7:
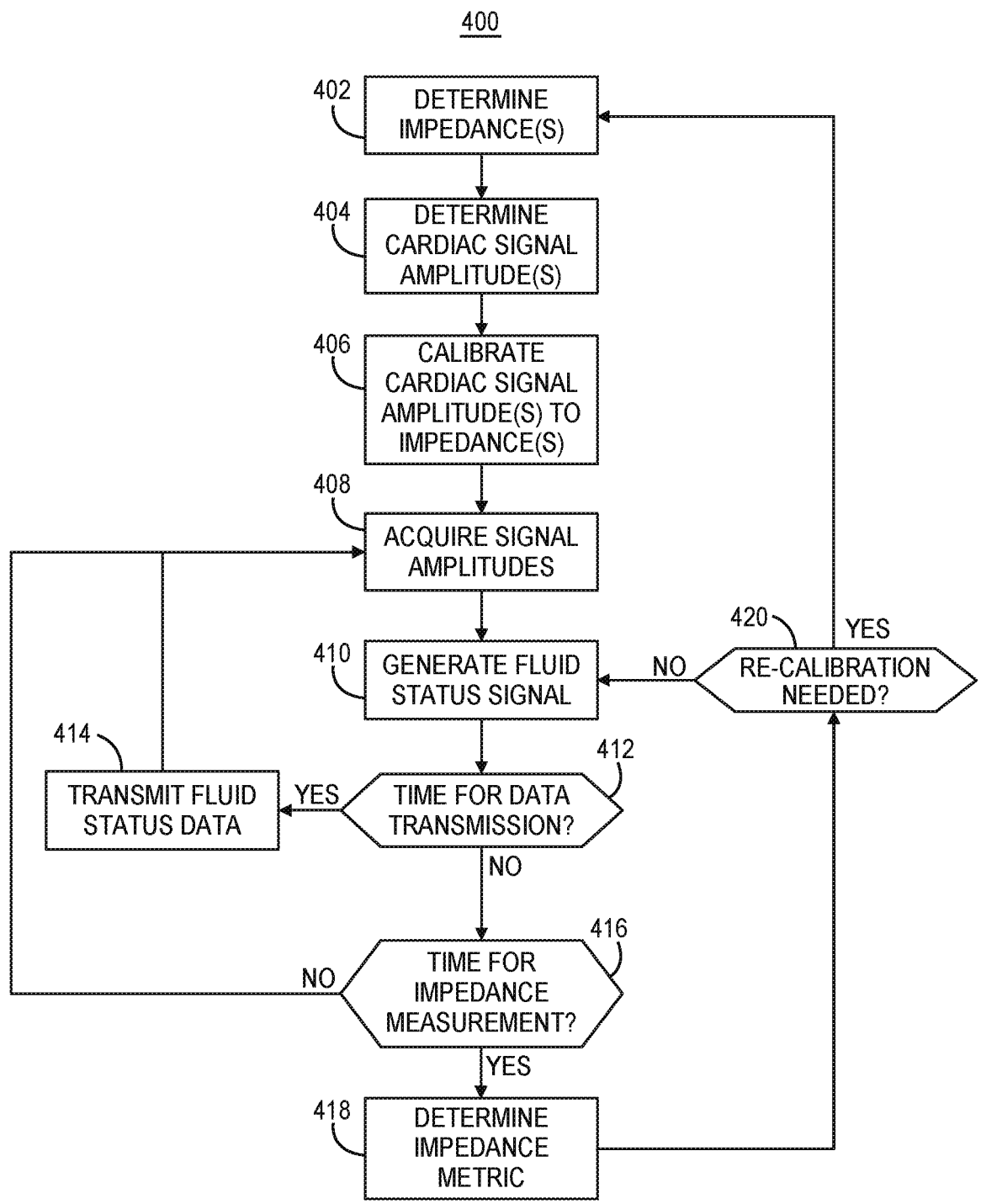
FIG. 7 is a flow chart of a method performed by a fluid status monitor according to one example.

FIG. 7 is a flow chart 400 of a method performed by a FSM according to one example. In the description that follows, reference is made primarily to FSM 14 of FIGS. 1 and 5, however the method of flow chart 400 may be performed by FSM 14 (FIG. 1), ICD 114 (FIG. 3), or ICD 214 (FIG. 4) as examples. At block 402, control circuit 80 controls impedance sensing circuit 84 to apply a drive current signal to a selected fluid status monitoring electrode vector. The fluid status monitoring electrode vector is between electrodes 28 and 30 in the example of FSM 14. When more than two electrodes are available, the fluid status monitoring electrode vector may be selected to obtain an impedance signal corresponding to a desired volume of tissue and associated body fluid compartments. For example, in the case of ICD 114, a fluid status monitoring electrode vector may include two electrodes carried by lead 116 or one electrode carried by lead 116 and the housing 115. The voltage signal developed across the fluid status monitoring electrode vector is passed from impedance sensing circuit 84 to control circuit 80. The voltage signal, e.g., the peak-to-peak voltage amplitude, may be recorded as the measurement of impedance in one example. In other examples, a voltage signal may be applied to a fluid status monitoring electrode and the resulting current may be recorded as a measurement of impedance. In still other examples, the voltage or current signal recorded from the fluid status monitoring electrode vector may be converted to an impedance measurement (or purely resistive measurement). The impedance measurement may be determined for a single frequency drive current signal, e.g. 8 KHz or other selected frequency, or two or more frequencies.

Numerous techniques may be used to obtain an impedance signal at block 402. Various examples of techniques that may be used in obtaining an impedance signal at block 402 are generally disclosed in U.S. Pat. No. 6,978,171

(Goetz, et al.), U.S. Pat. No. 7,986,994 (Stadler, et al.), U.S. Pat. No. 8,972,005 (Rasmussen, et al.), U.S. Pat. No. 8,428,717 (Wang, et al.) and U.S. Pat. No. 9,197,173 (Denison, et al.), all of which are incorporated herein by reference in their entirety. The particular method of acquiring an induced current or voltage signal correlated to the impedance of a volume of tissue may vary between embodiments. The particular method of obtaining an impedance signal that is utilized in the method of FIG. 7 and other flow charts presented herein will depend in part on the particular circuitry of the FSM that is available for generating a drive current (or voltage) signal and recording a resulting voltage (or current) signal. It is recognized that in some examples, the fluid status monitoring electrode vector may include a drive electrode pair and a recording electrode pair that is different than the drive electrode pair.

Before, during and/or after recording an impedance signal, control circuit 80 (or sensing circuit 86) may determine the amplitude of a cardiac electrical signal received by sensing circuit 86 at one or more time points during one or more cardiac cycles and during one or more respiration cycles at block 404. In one example, the maximum peak R-wave amplitude is determined for multiple cardiac cycles, which may or may not be consecutive, and the mean, median or a trimmed mean or median may be determined as a cardiac electrical signal amplitude measurement. Alternatively, one or more cardiac signal amplitudes determined at block 404 may be used individually instead of being combined in a mean or represented by a median amplitude.

Both the impedance signal and the cardiac electrical signal amplitudes may be acquired over two or more respiration cycles to reduce signal variation due to respiration. Modulation of the subcutaneous ECG signal amplitude due to respiration can be quite large, for example. Impedance signal changes due to respiration may be relatively smaller and may depend on the electrode location used to obtain the impedance signal. Modulation of the impedance and cardiac electrical signal amplitudes due to respiration may vary depending on electrode location, patient anatomy, respiratory volume and other factors. As such, cardiac electrical signal amplitudes and/or impedance signal amplitudes may be acquired over two or more respiration cycles and averaged to obtain respective impedance signal amplitude data points and cardiac electrical signal amplitude data points at blocks 402 and 404, respectively. For instance, the peak R-wave amplitudes and impedance signal amplitudes may be averaged over at least two respiration cycles or another predetermined number of respiration cycles, or a predetermined time interval, e.g., at least five seconds. In some examples, the cardiac electrical signal amplitudes are sampled over a predetermined time period that is expected to include at least two respiration cycles. For instance, R-wave amplitudes may be acquired for each cardiac cycle during a time interval of 10 to 12 seconds and averaged to obtain an R-wave amplitude used in a calibration procedure at block 406.

In some cases, the impedance and/or cardiac electrical signals may be subjected to noise or artifact. Control circuit 80 may be configured to detect noise in the electrical signals based on signal energy, number of signal peaks, or other noise detection criteria. If noise is detected, control circuit 80 may wait until noise is not being detected for collecting impedance signal and cardiac electrical signal amplitudes. In some examples, patient physical activity may cause variation or noise in the impedance and cardiac electrical signals. Control circuit 80 may monitor a signal from posture and activity sensor 85 for detecting patient activity. An activity count based on the number of threshold crossings of the activity sensor signal or another activity metric may be determined from the posture and activity sensor signal. Control circuit 80 may acquire impedance signal amplitudes and cardiac electrical signal amplitudes for fluid status monitoring, at block 402 and 404 respectively, during periods of low activity or rest as determined based on the patient activity metric.

In acquiring cardiac signal amplitudes at block 404, control circuit 80 may be configured to detect premature or ectopic beats to reject a cardiac cycle that includes a premature ventricular contraction or other abnormal beat. Detection of a premature ventricular contraction may be based on time intervals between R-wave sensed event signals received from sensing circuit 86 and/or cardiac signal waveform morphology analysis performed by control circuit 80. If a patient has a large number of premature beats, amplitudes of premature beats may be determined and stored separately from normal sinus R-wave amplitudes.

At block 406, control circuit 80 calibrates the cardiac signal amplitude(s) based on the impedance signal amplitudes. Control circuit 80 may determine a calibration formula or calibration look-up table based on sampled cardiac signal amplitudes, e.g., R-wave peak amplitudes, and impedance signal amplitudes. The calibration formula or look-up table can be used to adjust the cardiac signal amplitudes to match the impedance signal amplitudes (within an acceptable tolerance). For instance, at least two impedance metrics and two concurrently acquired cardiac signal amplitudes may be determined for determining a calibration formula for adjusting the cardiac electrical signal amplitudes. The adjustment may require one or more operations, for example multiplying the cardiac signal amplitude by a coefficient and/or adding a positive or negative constant, either to the cardiac signal amplitude or to the product of the cardiac signal amplitude and the coefficient. In other examples, multiple impedance metrics and corresponding cardiac signal amplitudes may be determined for generating a look-up table of calibrated cardiac electrical signal amplitudes over a desire range of impedance metrics.

Control circuit 80 may be configured to determine a calibration formula as a mathematical function that provides a best fit relationship between impedance measurements determined at block 402 and cardiac signal amplitudes determined at block 404. At least two impedance measurements and corresponding cardiac signal amplitudes may be used to determine a linear calibration formula for adjusting the cardiac signal amplitudes during fluid status monitoring. The calibration formula may be a linear function, e.g., including an offset (constant) that is added to or subtracted from the product of a cardiac signal amplitude and a coefficient. The offset is likely a non-zero value but may be zero in some instances. The coefficient may be greater than or less than one, but the coefficient may be one in some examples depending on the particular system and patient-dependent factors. The offset and coefficient may vary between patients and over time, e.g., as the patient gains or loses weight, the electrodes shift or other changes occur.

It is conceivable that a non-linear function may be determined as the best-fit relationship between multiple impedance measurements and contemporaneously acquired cardiac electrical signal amplitudes. Three or more impedance measurements and corresponding cardiac signal amplitudes may be used to determine a non-linear calibration formula. The determination of the best-fit relationship may be performed in stages to reduce processing burden required by the implantable FSM. For example, the control circuit 80 may determine a best linear fit for real-time patient monitoring. Control circuit 80 may perform post-processing to determine a best non-linear fit of the impedance and cardiac signal amplitude data and generate a fluid status signal from acquired cardiac signal amplitude data (and impedance data) based on the non-linear calibration formula. In some examples, the fluid status data acquired by control circuit 80 may be transmitted to an external device, e.g., external device 40 shown in FIG. 1, for the post-processing determination of a non-linear calibration formula. A processor of external device 40 or the central database 50 may perform the post-processing to determine a best non-linear fit of the impedance and cardiac signal amplitude data and generate a fluid status signal including cardiac electrical signal amplitudes adjusted according to the non-linear calibration model for display to a clinician.

In some examples, the calibration relationship may be established and programmed into the FSM using external device 40 or may be stored in memory 82 at the time of FSM manufacture. The calibration relationship may be established based on empirical, clinical data for a given FSM and fluid status monitoring electrode vector. In other examples, the calibration relationship is determined by the control circuit 80 after deployment for monitoring a patient's fluid status and stored in memory 82. An initial or starting calibration relationship may be stored in memory 82, e.g., based on empirical clinical data, and the calibration relationship (stored as a formula or a look-up table) may be adjusted and updated as impedance and cardiac electrical signal amplitude data are acquired over time from a given patient and over a range of fluid status conditions.

Control circuit 80 may be configured to determine one calibration or relationship between cardiac signal amplitudes and impedance measurements when the cardiac signal amplitudes are acquired during intrinsic cardiac cycles. Control circuit 80 may determine a second, different calibration or relationship between cardiac signal amplitudes and impedance measurements when the cardiac signal amplitudes are acquired during paced cardiac cycles. Since the R-wave may have a different amplitude during pacing than during an intrinsic rhythm, control circuit 80 may determine two different calibrations for adjusting cardiac signal amplitudes acquired during sensing and during pacing. In the example of FSM 14, which is illustrated as a monitoring only device with no therapy delivery capabilities, control circuit 80 may be configured to distinguish between paced cardiac cycles and intrinsic cardiac cycles based on detection of a pacing pulse or morphology of the cardiac electrical signal. In the case of a FSM capable of delivering cardiac pacing, e.g., FSM 314 of FIG. 6, control circuit 80 distinguishes between paced cardiac cycles and intrinsic cardiac cycles based on when therapy circuit 90 delivers a pacing pulse and when sensing circuit 86 passes sensed R-wave signals to control circuit 80.

If a patient has a large number of premature beat amplitudes stored separately from normal sinus R-wave amplitudes, two different calibration relationships may be determined. One calibration relationship may be determined based on the relationship between the premature beat amplitudes and the impedance metrics, and another calibration relationship may be determined based on the relationship between the normal sinus R-wave amplitudes and the impedance metrics.

The calibration process may include determining a predetermined minimum number of impedance metrics and corresponding cardiac signal amplitudes. As the number of impedance metrics and cardiac signal amplitudes used to establish the calibration relationship is increased, the confidence in the correlation between the calibrated cardiac signal amplitude values and actual impedance (and therefore fluid status) may increase.

In some examples, two or more impedance measurements may be acquired at block 402, along with corresponding cardiac signal amplitudes at block 404, until the range of the impedance measurements meets a predetermined minimum range. As the range of the impedance measurements used to establish the calibration relationship increases, the confidence in the correlation between calibrated cardiac signal amplitude values and the actual impedance may increase.

At block 408, after establishing the calibration relationship, control circuit 80 acquires cardiac electrical signal amplitudes according to a fluid status monitoring protocol. In some examples, the R-wave peak amplitude is sampled on a beat-by-beat basis. A running average of the R-wave peak amplitude may be determined, e.g., over 3, 5, 8, 12 or other selected number of R-wave peak amplitudes. The R-wave amplitudes may be averaged over one or more respiration cycles as described above to account for modulation of the cardiac electrical signal amplitude due to respiration. The averaged R-wave peak amplitude may be determined as the cardiac signal amplitude that is adjusted to obtain a fluid status metric.

The fluid status monitoring protocol may involve acquiring cardiac signal amplitudes once per hour, once every four hours, once every eight hours, once every 12 hours, once per day, or other predetermined periodic monitoring schedule. The cardiac signal amplitude may be determined from a single cardiac cycle according to the monitoring protocol or averaged from a predetermined number of cardiac cycles or a variable number of cardiac cycles occurring over a predetermined number of respiration cycles or a predetermined time interval.

At block 410, each cardiac signal amplitude (which may be an average value) is converted to a fluid status metric using the calibration determined at block 406. The calibrated cardiac signal amplitude becomes a sample point of the fluid status signal at block 410. The FSM 14 may be interrogated by an external device and/or programmed to transmit the fluid status signal at a specified time, e.g., once per day or more or less often. If it is time to transmit the fluid status signal, as determined at block 412, the fluid status data is transmitted at block 414 to an external device, e.g., external device 40 (FIG. 1). The transmitted data includes one or more calibrated cardiac signal amplitudes as fluid status metrics which may be assembled over time to generate a fluid status signal. The fluid status metrics and a corresponding generated fluid status signal may include one or more points generated from impedance measurements, e.g., including the first and/or last impedance measurement(s) used to calibrate the cardiac signal amplitudes and any additional impedance measurements obtained during the fluid status monitoring started at block 408.

If it is not time to transmit data, control circuit 80 may determine if it is time to acquire an impedance measurement at block 416. As cardiac signal amplitudes are being acquired according to a fluid status monitoring protocol, impedance metrics may be acquired periodically, for example on a less frequent schedule than cardiac signal amplitudes. The impedance metrics may be acquired to verify or update the calibration of the cardiac signal amplitudes. If it is not time for an impedance measurement ("no" branch of block 416), cardiac signal amplitudes continue to be acquired and adjusted according to the previously determined calibration for generating a fluid status signal. If it is time for an impedance measurement, control circuit 80 controls impedance sensing circuit 84 to acquire an impedance signal at block 418 and determines a verification impedance metric from the impedance signal. The verification impedance metric may be an average amplitude determined from the impedance signal over one or more cardiac cycles, over one or more respiration cycles or over a predetermined time interval, e.g., 10 seconds.

At block 420, control circuit 80 may compare the verification impedance metric to one or more most recent or simultaneously acquired calibrated cardiac signal amplitude(s) at block 420 to determine if re-calibration is needed. For example, if the calibrated cardiac signal amplitude and the verification impedance metric are within a predetermined threshold difference of each other, re-calibration is not performed. The match between the calibrated cardiac signal amplitude and the verification impedance metric suggests that the previously determined calibration relationship is still valid. The calibration relationship may be re-determined (return to block 402) in response to the verification impedance metric being greater than a threshold difference from one or more calibrated cardiac signal amplitudes.

In other examples, each time an impedance metric is obtained, control circuit 80 may return to block 406 to re-determine a calibration relationship of contemporaneously acquired cardiac signal amplitudes and impedance metrics. Impedance metrics may be obtained once per day or less often, as an example, for re-calibrating the cardiac signal amplitudes if needed.

Additionally, or alternatively, the difference between calibrated cardiac signal amplitudes may be determined at block 420. A relatively large change in the cardiac signal amplitude may indicate a change in fluid status but may be caused by a change in patient posture or other condition. If a threshold difference or slope between two of the calibrated cardiac signal amplitudes is detected at block 420, the calibration relationship may be updated by returning to block 402 to acquire the required number of impedance and cardiac signal amplitude data points, which may include recently acquired cardiac signal amplitudes and impedance metrics. After re-calibration, cardiac electrical signal amplitudes continue to be acquired according to the fluid status monitoring protocol and the fluid status signal is generated at block 410 using the updated calibration relationship.

Figure 8:
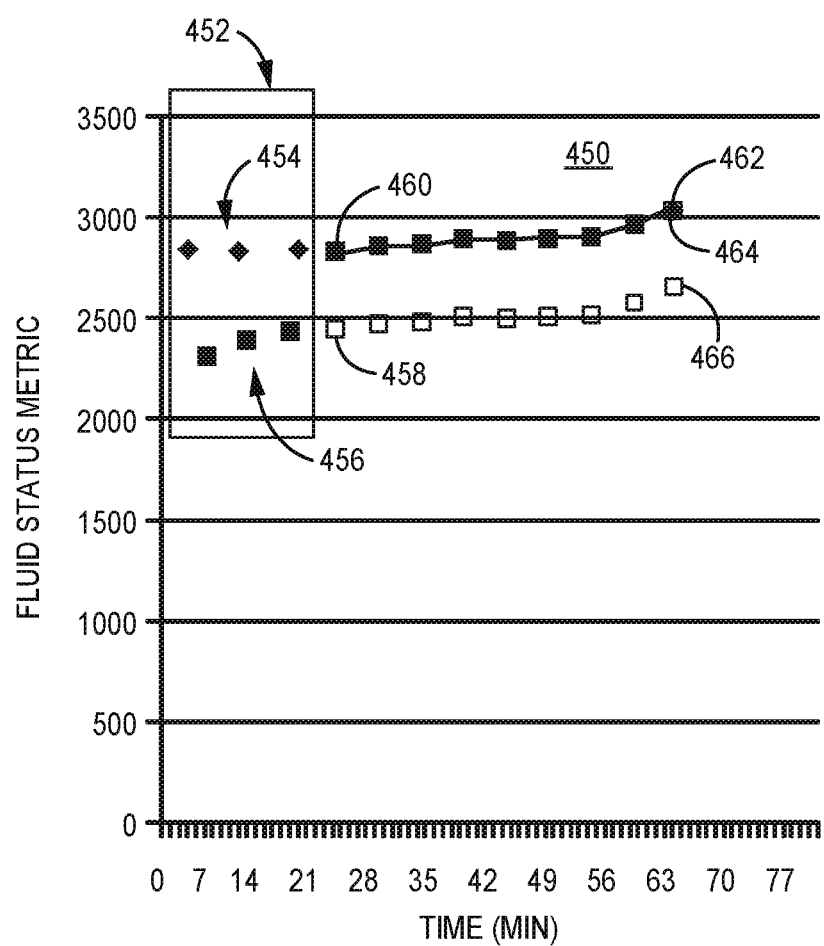
FIG. 8 is a diagram of a fluid status signal that may be generated by a fluid status monitor according to one example.

FIG. 8 is a diagram of a fluid status signal 450 that may be generated by a FSM according to one example. Control circuit 80 may control impedance sensing circuit 84 to obtain impedance metrics 454 during a calibration interval 452. During the calibration interval 452, control circuit 80 also acquires cardiac electrical signal amplitudes 456. In one example, multiple impedance metrics 454 are determined, and multiple cardiac electrical signal amplitudes 456 are determined simultaneously or at least within the same calibration interval 452. In the example shown, three impedance metrics 454 and three cardiac electrical signal amplitudes 456 are depicted, however it is to be understood that less than three or more than three impedance and cardiac electrical signal amplitude data points may be determined during calibration interval 452 for use in determining the calibration relationship. The calibration interval 452 may be a portion of one minute, several minutes, one hour, several hours, one day or other predetermined time interval during which impedance and cardiac electrical signal amplitude data is acquired for establishing the calibration relationship. The calibration interval 452 may be a fixed time interval. In other examples, the calibration interval 452 is a variable time interval that is extended until a desired range of the impedance and/or a minimum number of data points are acquired.

Each of the impedance metrics 454 may represent an average amplitude determined from the impedance signal (e.g., a voltage signal) received by control circuit 80 from impedance sensing circuit 84. The average amplitude may be determined by sampling the impedance signal over a predetermined time interval, e.g., 10 seconds, over a predetermined number of cardiac cycles, or a predetermined number of respiration cycles. The cardiac electrical signal amplitudes 456 may each represent the peak amplitude of an R-wave or peak-to-peak R-wave (or another other fiducial point) determined from a single cardiac cycle. In other examples, each cardiac electrical signal amplitude 456 may represent a mean or median of a predetermined number of R-wave amplitudes or a running average of a predetermined number of R-wave amplitudes. For instance, each cardiac electrical signal amplitude 456 during calibration interval 452 may be an average of the peak R-wave amplitudes determined beat-by-beat for each cardiac cycle occurring over the same time interval that a corresponding impedance metric 454 is determined or over the time interval between two consecutive impedance measurements. In other examples, each cardiac electrical signal amplitude 456 is an average of a predetermined number of R-wave peak amplitudes determined before and after each impedance measurement 454. In yet another example, each cardiac electrical signal amplitude 456 is an average of a variable number of R-wave peak amplitudes determined over a fixed time interval.

During the calibration interval 452, the impedance metrics 454 and the cardiac electrical signal amplitudes 456 may be determined at regular time intervals. For example, if the calibration interval 452 is scheduled to be 24 hours, the impedance metrics 454 and cardiac electrical signal amplitudes 456 may be determined once per hour. Shorter or longer calibration intervals may be used with higher or lower frequencies of impedance and cardiac electrical signal amplitude acquisition. Various methods may be conceived for acquiring impedance metrics 454 and corresponding cardiac electrical signal amplitudes 456 over a calibration time interval 452 for use in determining a relationship between the magnitude of the impedance metrics 454 and the cardiac electrical signal amplitudes 456.

It is recognized that impedance and cardiac electrical signal amplitude data may be acquired over two or more calibration time intervals for establishing the calibration relationship. For instance, if a range of the amplitude of the impedance measurements 454 (and/or cardiac signal amplitudes 456) is less than a minimum desired range within one calibration time interval 452, data may be acquired over a second calibration time interval or the calibration time interval 452 may be extended to acquire more data points. Impedance metrics and cardiac electrical signal amplitudes obtained over two or more calibration time intervals may be combined to determine the calibration relationship and improve the confidence of the calibration relationship.

In some examples, control circuit 80 may monitor patient posture and/or activity based on the signal(s) received from posture and activity sensor 85 to promote calibration data acquisition during periods of stable patient posture and activity. If a change in posture and/or activity is detected, the calibration time interval 452 may be restarted or delayed. When calibration data from multiple calibration time intervals is being combined for determining a calibration relationship, control circuit 80 may verify that each calibration interval is associated with a common patient posture and patient activity level, e.g., a resting patient activity level.

Control circuit 80 may determine a mathematical relationship between the impedance measurements 454 and the cardiac electrical signal amplitudes 456 acquired during the calibration interval 452 to establish a calibration relationship. The calibration relationship may include a linear formula or a non-linear formula. In other examples the calibration relationship is established as a look-up table. After the calibration interval 452, control circuit 80 monitors fluid status by acquiring cardiac electrical signal amplitudes 458 (open squares). Each cardiac signal amplitude may represent an amplitude acquired from a single cardiac cycle according to a monitoring protocol or an average or median of multiple cardiac signal amplitudes determined over a predetermined number of cardiac or respiration cycles or over a fixed time interval, which may include a variable number of cardiac cycles. Each cardiac electrical signal amplitude 458 is adjusted according to the calibration relationship to generate a fluid status metric 460 (solid squares). A fluid status metric 460 may be determined at predetermined time intervals according to a monitoring protocol. For instance, an average peak R-wave amplitude may be determined over every 10 to 20 cardiac cycles and converted to a fluid status metric according to the calibration relationship. In various examples, a fluid status metric may be determined once per minute, once every five minutes, once per hour, or every X hours.

Periodically, an impedance metric 462 is determined to check the calibration of the cardiac electrical signal amplitude and/or to improve the linear or non-linear best fit calibration formula or update a calibration look-up table. In the example shown in FIG. 8, fluid status metric 464 determined by adjusting the most recent cardiac electrical signal amplitude 466 is well-correlated with the impedance metric 462. As long as the fluid status metric 464 is within an acceptable range, e.g., ±10 percent, of a corresponding impedance metric 462, the calibration relationship may be deemed valid. If the fluid status metric 464 is different than the impedance metric 462, based on the predetermined acceptable range, control circuit 80 may start a new calibration interval 452 to collect additional impedance metrics and cardiac electrical signal amplitudes to improve or reestablish the calibration relationship. As described below, an impedance metric 462 may be performed in response to detecting a change in patient body posture to verify that the calibration relationship is still valid and, if not, re-determine the relationship between impedance measurements and cardiac electrical signal amplitudes in the new patient posture.

The fluid status metrics 460 may be used to generate the fluid status signal 450 which may be transmitted to an external device for display to a clinician. In some examples, interpolation between points defined by the calibrated fluid status metrics may be performed to generate a continuous fluid status signal 450 as shown. In other examples, the fluid status signal 450 may include the calibrated fluid status metric points without interpolation. The fluid status signal 450, which may include both the fluid status metric points 460 and the impedance measurements 454 and/or 462, may be transmitted to an external device for display to a clinician. In some examples, the non-calibrated cardiac electrical signal amplitudes 456 determined during the calibration interval 452 and/or the non-calibrated cardiac electrical signal amplitudes 458 may also be transmitted as fluid status data during a telemetry session with an external device.

In the example of FIG. 8, the fluid status signal 450 increases with decreasing fluid present in the measurement volume (as impedance and cardiac signal amplitude increase). Fluid status signal 450 decreases with increasing fluid present in the measurement volume (as impedance decreases and cardiac signal amplitude decreases). In other examples, control circuit 80 may invert the fluid status signal 450 so that as fluid in the measurement volume increases the fluid status signal 450 also increases to provide a more intuitive representation of fluid status to a clinician.

As shown by the example of FIG. 8, fluid status metrics acquired over time may include impedance metrics 462 determined relatively infrequently, e.g., once per hour or once per day, with calibrated cardiac electrical signal amplitudes determined relatively frequently, such as several times per minute, once per minute, several times per hour, or hourly, as examples. In this way, monitoring of a patient's fluid status can be performed in a relatively high frequency, energy efficient manner by reducing the frequency of required impedance measurements for monitoring fluid status.

Figure 9:
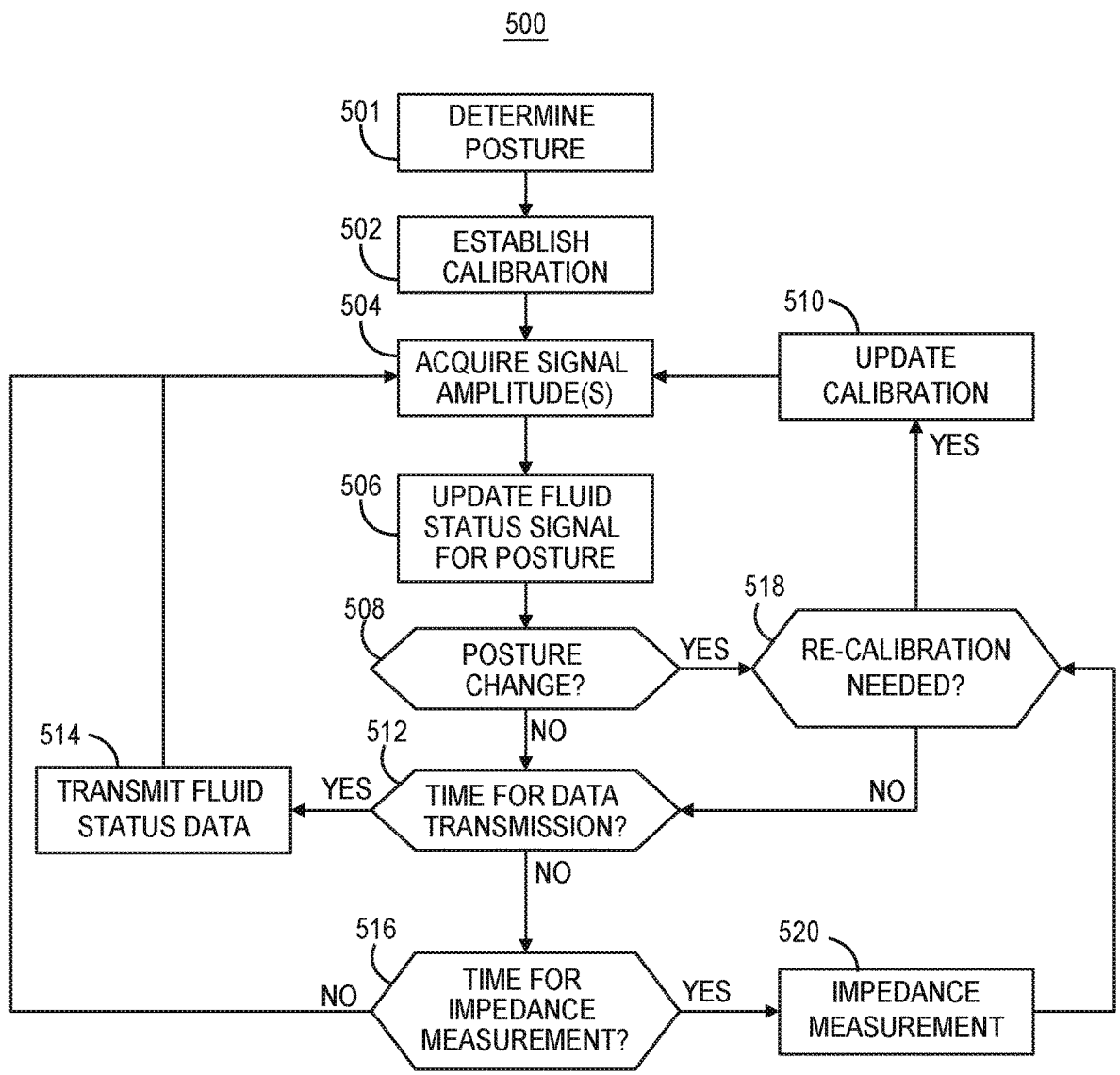
FIG. 9 is a flow chart of a method performed by a fluid status monitor according to another example.

FIG. 9 is a flow chart 500 of a method performed by FSM 14 (or 314) according to another example. At block 501, control circuit 80 may determine the patient's body posture based on a signal from posture and activity sensor 85. In some examples, body posture is determined using a combination of the vector signals received from each axis of a three-dimensional accelerometer. The posture may be determined as an upright position (e.g., standing or sitting) or a non-upright position (e.g., laying or reclined). At block 502, control circuit 80 establishes the calibration relationship for adjusting cardiac signal amplitudes based on impedance metrics and stores calibration parameters in memory 82 for the detected patient body posture.

At block 504, control circuit 80 acquires cardiac electrical signal amplitudes according to a fluid status monitoring protocol, e.g., according to any of the examples described above. At block 506, control circuit 80 adjusts the cardiac electrical signal amplitudes, either in real time as they are acquired or in post-processing, according to the calibration relationship established at block 502. A fluid status signal may be generated and stored for the detected posture using the calibrated cardiac electrical signal amplitudes acquired over time.

At block 508, control circuit 80 monitors the posture sensor signal for detecting a change in the patient body posture. A change in patient body posture may be detected in response to a threshold change in one or more of the individual vector signals received from a multi-axis accelerometer included in posture and activity sensor 85 or a threshold change in a combination of the three vector signals. For example, control circuit 80 may use the posture and activity sensor signal to at least discriminate between an upright position, e.g., standing or sitting, and a substantially horizontal or reclined position. Patient body posture monitoring at block 508 is shown to be performed sequentially after blocks 504 and 506, however, it is to be understood that posture monitoring may be occurring concurrently with the acquisition of cardiac electrical signal amplitudes. A change in patient body posture may be detected at block 508 based on comparing the posture sensor signal to predetermined criteria established for detecting a posture change.

In some examples the type of posture change may be determined as a "major" posture change or a "minor" posture change. A "major" posture change may be defined as a posture change that results in a major change in the center of gravity of the body, e.g., from an upright position to a horizontal position. The body plane or axis along which the center of gravity is aligned changes from a vertical, e.g., sagittal or frontal plane, to a horizontal, e.g., a transverse plane, when changing positions from an upright to a laying posture, as an example of a major posture change. Posture changes that do not result in a major change in the center of gravity, for example from standing to sitting or from laying prone to supine, may be considered "minor" posture changes. The body plane or axis along which the center of gravity is aligned does not change significantly in a minor posture change. For instance, a major posture change may be from an upright (standing or sitting) position to a laying position or vice versa. A minor posture change is change from one laying position to another or from one upright position to another.

If a posture change is detected at block 508, control circuit 80 may determine if re-calibration is needed at block 518. In one example, re-calibration is performed after every posture change detection. In other examples, re-calibration is performed after every major posture change detection and may or may not be performed after a minor posture change detection. In still other examples, when a major or minor posture change is detected, other criteria are applied at block 518 to determine if re-calibration is needed. Other criteria applied at block 518 may include detecting a threshold change in the cardiac electrical signal amplitudes determined prior to and after the posture change. In other examples, an impedance metric may be determined in response to detecting the posture change and compared to a most recent preceding impedance metric and/or the most recent calibrated cardiac electrical signal amplitude(s). If the impedance metric determined after the posture change is greater than a threshold difference from a preceding impedance metric (prior to the posture change) and/or from the calibrated cardiac electrical signal amplitudes (determined after the posture change), control circuit 80 may determine that re-calibration is needed. Otherwise, re-calibration is not needed.

Re-calibration may include storing a new calibration relationship, or updating a previously stored calibration relationship, corresponding to the newly detected posture. The previously determined calibration relationship established prior to detecting the change in patient body posture may continue to be stored for use when a change back to the first body posture is detected. When a change back to the first body posture is detected, the first calibration relationship may be updated or re-established. In this way, a calibration relationship may be stored in memory 82 for multiple patient body postures for use by control circuit 80 in adjusting cardiac electrical signal amplitudes when a respective patient body posture is being detected.

In one example, control circuit 80 is configured to detect a posture change at block 508, and perform a re-calibration at block 518. In another example, control circuit 80 is configured to detect a posture change at block 508 and determine if the posture change is a major posture change or a minor posture change. Control circuit 80 performs a re-calibration at block 518 in response to determining that the posture change is a major posture change. In response to determining that the posture change is a minor posture change, control circuit 80 determines if other re-calibration criteria are met based on the impedance signal and/or the cardiac electrical signal. Control circuit 80 re-determines or updates the calibration relationship at block 518 in response to a minor posture change being detected and other re-calibration criteria being met. As described above, determining that the other re-calibration criteria are met may include detecting a threshold impedance change between an impedance metric determined after the minor posture change and an impedance metric determined before the posture change, determining a threshold difference between an impedance metric after the minor posture change and one or more calibrated cardiac electrical signal amplitudes determined after the minor posture change, and/or detecting a threshold change in cardiac electrical signal amplitudes (calibrated or non-calibrated) determined before and after detecting the minor posture change.

At block 510, the calibration relationship is updated based on at least one new impedance measurement and one or more cardiac electrical signal amplitudes. At least two or more impedance measurements and multiple cardiac electrical signal amplitudes may be acquired after the posture change to update the calibration relationship. Impedance may be less affected by posture change than cardiac signal amplitude. Accordingly, in some examples, an impedance metric obtained in response to the detected posture change may be used in combination with one or more impedance metrics obtained prior to the detected posture change and multiple cardiac electrical signal amplitudes obtained prior to the posture change for calibrating the cardiac electrical signal amplitudes acquired prior to the posture change if needed. For example, if a posture change is detected before a required number of impedance measurements are obtained for calibrating the cardiac electrical signal amplitudes acquired before the posture change, an impedance metric obtained immediately after the posture change may be used in combination with one or more impedance metrics obtained before the posture change to calibrate the cardiac electrical signal amplitudes.

The calibration performed at block 510 may include generating a look-up table of calibration parameters, e.g., a slope and/or offset, versus posture. The slope and/or offset for each posture can be determined from a linear fit of cardiac electrical signal amplitudes versus impedance metrics for a given posture. Linear fit can be updated to include more calibration data points each time the patient resumes a given posture (e.g., when a change to a given posture is detected from the posture and activity sensor signal). The calibration parameters may be updated each time more calibration data points (cardiac electrical signal amplitude vs. impedance metric data points) are added. The calibration parameters may be based on a maximum number of data points to avoid excessive processing burden each time calibration data points are acquired. Once a maximum number of data points has been reached, the calibration relationship is not necessarily updated unless other re-calibration criteria are met, e.g., detecting a threshold change in impedance metrics and/or cardiac electrical signal amplitudes.

In other examples, if a predetermined maximum time interval has elapsed without updating the calibration relationship for a give posture, the calibration relationship may be updated when the given posture is detected. A maximum time interval may be one week or one month, as examples, to account for gradual changes such as patient weight gain, electrode shifting or other conditions that may influence the calibration relationship.

Cardiac electrical signal amplitudes acquired from the time that the posture change detection is made are adjusted according to the updated (or newly established posture-specific) calibration relationship. Control circuit 80 continues to acquire cardiac electrical signal amplitudes at block 504 and stores the resulting fluid status metrics at block 506. A fluid status signal may be updated at block 506 for the currently detected posture. As described above in conjunction with FIG. 7, FSM 14 (or FSM 314) may receive an interrogation command or programmed time for transmitting fluid status data may be reached at block 512. The fluid status data acquired since the last data transmission may be transmitted to an external device at block 514.

In addition to monitoring for posture changes, control circuit 80 may be configured to periodically determine an impedance measurement at block 520 during fluid status monitoring and for updating the calibration relationship, whether or not a posture change has been detected. Impedance metrics may be determined infrequently compared to cardiac electrical signal amplitude monitoring to conserve battery longevity of power source 98. If it is time to periodically determine impedance, control circuit 80 determines an impedance metric from the impedance sensing circuit signal at block 520. The impedance metric may be used in generating the fluid status signal at block 508 and/or verifying that the calibration relationship is still valid at block 518 using any of the methods described above.

In some examples, a single fluid status signal is generated for all postures by adjusting the calibration of the cardiac electrical signal amplitudes acquired during different postures. When fluid status data is transmitted to an external device, control circuit 80 may transmit a single fluid status signal that is generated for all body postures. In other examples, a fluid status signal is generated for each patient body posture detected according to a calibration relationship determined for each posture. When fluid status data is transmitted to an external device, data for multiple fluid status signals may be transmitted so that one fluid status signal may be displayed for each body posture that is detected. In some examples, one fluid status signal is generated for a first type of patient body posture and a second fluid status signal is generated for second type of patient body posture. Each type of body posture may include multiple postures which represent minor posture changes relative to gravity, e.g., all non-upright laying positions or all upright vertical positions, or only a first group of patient body postures and the second group of body postures representing a major posture change. For instance, if upright postures (e.g., standing and sitting) are discriminated from non-upright postures (e.g., reclined or lying), two fluid status signals may be generated.

Figure 10:
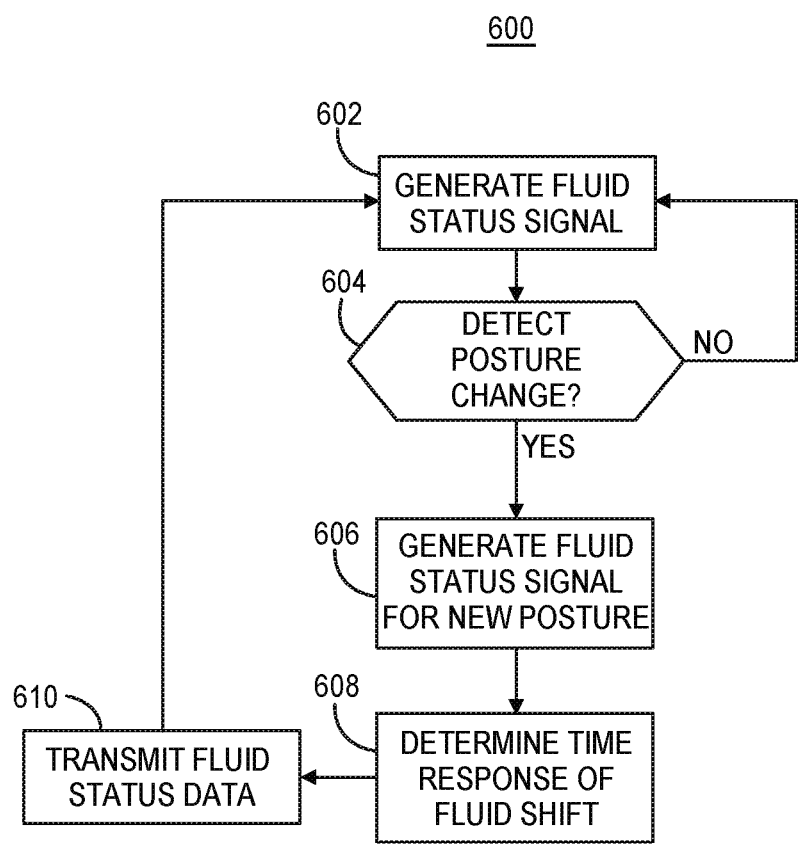
FIG. 10 is a flow chart of a method that may be performed by a fluid status monitor according to yet another example.

FIG. 10 is a flow chart 600 of a method that may be performed by a FSM according to another example. At block 602, control circuit 80 generates a fluid status signal by acquiring cardiac electrical signal amplitudes and calibrating the cardiac signal amplitudes according to a relationship between cardiac signal amplitude and impedance metrics. The patient body posture may be determined so that the fluid status signal and corresponding calibration of the cardiac electrical signal amplitudes are stored in memory for the corresponding patient body posture.

Control circuit 80 monitors the signal from posture and activity sensor 85 at block 604 for detecting a change in patient body posture. As described above, control circuit 80 may determine if the change in patient body posture is a major posture change corresponding to a major change in the patient's center of gravity. When a major change in body posture is detected, control circuit 80 begins generating a fluid status signal for the new posture at block 606. One fluid status signal may be generated for all upright postures combined and another fluid status signal may be generated for all non-upright (e.g., laying) postures combined. These fluid status signals may be appended with new data each time the corresponding major posture is detected. Generating the fluid status signal after the posture change detection may include determining a new calibration relationship based on impedance measurements as described above. In other examples, control circuit 80 may retrieve a previously established calibration relationship stored in memory 82 for the newly detected posture.

At block 608, control circuit 80 may monitor a time response of a change in the fluid status signal. As patient body posture changes, fluid shifts from one body region to another may occur and/or fluid shifts between interstitial and intravascular compartments may occur. The time response of a fluid shift after a postural change may provide diagnostic or prognostic information relating to the patient's ability to regulate fluid distribution through the body. The time response of a fluid shift determined at block 608 may include a determination of a time interval from the time of the detected posture change until the fluid status signal reaches a steady state, increases to a maximum or decreases to a minimum. The time response may alternatively be determined as a slope of the fluid status signal over one or more time intervals following the detected posture change. In other examples, the time response may include determining a time interval for the fluid status signal to increase to a maximum and return to a level preceding the posture change or the time for a decrease to a minimum and return to a level preceding the posture change, as examples.

The time response may occur over minutes or hours, and, in some instances, a posture change may occur again prior to the fluid shift reaching a steady state. In this case, a slope of the fluid shift may be determined as the time response at block 608. If the posture changes again before the time response can be determined, e.g., before a minimum time interval over which a fluid status signal slope is determined, the time response may go undetermined for that posture change. In some examples, the most significant fluid shift may occur when a patient changes from an upright position to a laying position or vice versa. As such, in some examples, the time response of a fluid shift may be determined at least once or twice daily, when a patient transitions from an upright position to a laying position when going to bed and/or when the patient transitions from a laying position to an upright position when getting up in the morning. It is expected that the newly detected posture associated with going from upright to laying upon going to bed or from laying to upright upon getting up from bed will be sustained for a relatively long period of time, e.g., one hour or more, allowing adequate time to observe changes in the fluid status signal associated with a posture-induced fluid shift.

The time response data may be transmitted to an external device at block 610 and may be presented in a graphical or tabular manner. In some examples, both the fluid status signal data and fluid shift response times are transmitted to the external device for generating a fluid status data display to a clinician. The fluid status signal data obtained during upright postures may be grouped for generating an upright fluid status signal and time response to changes to the upright posture. The fluid status signal data obtained during non-upright postures (e.g., all laying postures) may be grouped for generating a non-upright fluid status signal and time response to changes to the non-upright posture.

Figure 11:
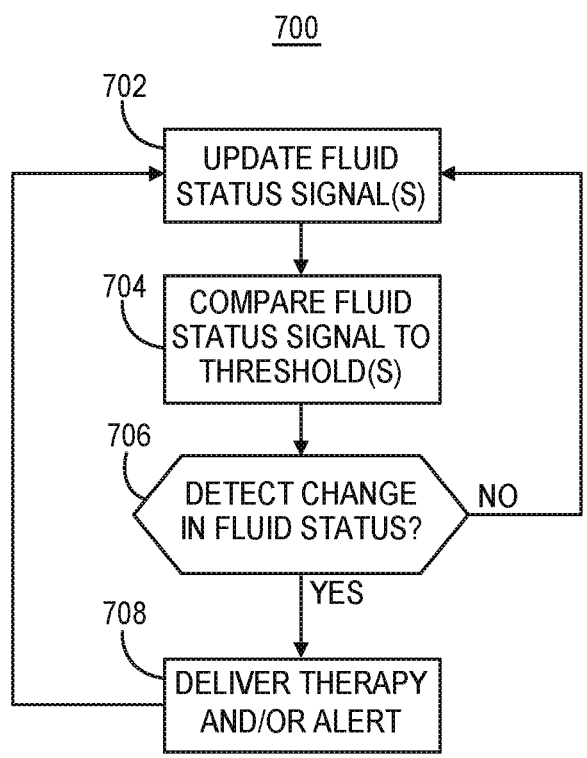
FIG. 11 is a flow chart of an example method that may be performed by a fluid status monitor capable of therapy.

FIG. 11 is a flow chart 700 of a method that may be performed by FSM 14 or 314 in some examples. At block 702, the fluid status signal is generated and updated as described above. At block 704, the fluid status signal amplitude, slope or other feature may be compared to criteria for detecting a fluid status condition. For example, the amplitude or slope may be compared to one or more thresholds for detecting one or more fluid status conditions. Depending on the clinical application, one or more fluid status conditions may be detected such as fluid retention due to heart failure, fluid retention due to anemia, overdiuresis, pulmonary edema, dehydration, and trauma. Control circuit 80 may detect a change in fluid status based on an amplitude threshold crossing of the fluid status signal, a threshold slope being detected, and/or threshold change in the slope being detected, for example. In response to detecting a change in fluid status, the control circuit 80 may control telemetry circuit to transmit fluid status data or an alert signal to an external device at block 708. Additionally or alternatively, when the FSM includes therapy delivery capabilities, e.g., FSM 314 of FIG. 6, control circuit 80 may control therapy circuit 90 to deliver or adjust a therapy in response to detecting the change in the fluid status. The therapy delivery or adjustment may include turning on or turning off a pacing therapy or switching a pacing mode, adjusting a ventricular pacing rate, adjusting an atrioventricular pacing interval, or adjusting the timing of cardiac resynchronization therapy pacing pulses.

The techniques described in conjunction with the flow charts and diagrams presented herein may be performed by a medical device system, in which some aspects of the disclosed techniques are performed by one or more implantable medical devices, e.g. FSM 14, ICD 114 and/or ICD 214, and other aspects are performed by another implantable medical device and/or an external device, e.g., external device 40, in some examples. For instance, FSM 14, ICD 114 or ICD 214 may generate fluid status signal data according to the techniques disclosed herein by determining impedance metrics and cardiac signal amplitudes at desired time intervals and/or over desired impedance metric ranges for enabling determination of a calibration relationship. Updating the fluid status signal(s) at block 702 may include transmitting the cardiac signal amplitudes and impedance metrics, which may be referred to as "raw fluid status signal data," to another medical device, e.g., from FSM 14 to external device 40, for determination of the calibration relationship and generating and updating the fluid status signal(s) by external device 40. External device 40 may generate/update a fluid status signal by determining the calibration relationship from the raw fluid status signal data and adjusting the cardiac signal amplitudes according to the calibration relationship. At block 704, the external device 40 may compare the updated fluid status signal to one or more thresholds at block 704 to detect a change in fluid status at block 706.

At block 708, the external device 40 may generate an alert and/or determine an appropriate therapy adjustment in response to detecting the change in fluid status. For example, processor 52 (FIG. 1) of external device 40 may select a therapy adjustment command in response to detecting the change in fluid status and control telemetry unit 58 to transmit the therapy adjustment command to a therapy delivery device, e.g., to ICD 114 or ICD 214. The therapy delivery device is configured to receive the therapy adjustment command and deliver the therapy to the patient according to the therapy adjustment command, e.g., by starting, stopping or adjusting a pacing therapy or other cardiac electrical stimulation therapy. In some examples, the raw fluid status signal data may be transmitted from FSM 14 directly to a therapy delivery device, e.g., ICD 114 or ICD 214, and the control circuit of the therapy delivery device may be configured to generate the fluid status signal, comparing the signal to one or more thresholds, and generating an alert and/or determining a therapy adjustment and delivering the adjusted therapy to the patient.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Illustrative Embodiments

While the present disclosure is not so limited, an appreciation of various aspects of the disclosure of the present application will be gained through a discussion of some illustrative embodiments provided below.

Various illustrative embodiments are directed to atrioventricular synchronous pacing.

In illustrative embodiment 1, a medical device is disclosed. The medical device, comprises:
a sensing circuit configured to receive a cardiac electrical signal via electrodes coupled to the medical device;
an impedance sensing circuit configured to apply a drive signal to electrodes coupled to the medical device and sense a resultant impedance signal;
a telemetry circuit configured to transmit fluid status data to another medical device; and
a control circuit coupled to the sensing circuit, the impedance sensing circuit and the telemetry circuit, the control circuit configured to:
determine a plurality of impedance metrics from the impedance signal;
determine a first plurality of amplitudes from the cardiac electrical signal;
determine a first calibration relationship between the plurality of impedance metrics and the first plurality of amplitudes;
determine a second plurality of amplitudes from the cardiac electrical signal; and generate fluid status signal data by adjusting the second plurality of amplitudes according to the determined first calibration relationship.

In illustrative embodiment 2, the device further comprises a power source coupled to the control circuit and the impedance sensing circuit for generating the drive signal, wherein the power source life is conserved by using the first calibration relationship compared to implantable medical devices that solely use the impedance signal to acquire fluid status signal data.

In illustrative embodiment 3, the device of embodiment 2, wherein the power source is a battery.

In illustrative embodiments 4, the device of any of embodiments 1-3, wherein the control circuit is further configured to control the telemetry circuit to transmit the fluid status signal data to another medical device for generating a display of the fluid status signal data.

In illustrative embodiments 5, the device of any of embodiments 1-4, wherein the control circuit is configured to determine each of the first plurality of amplitudes and each of the second plurality of amplitudes by determining an R-wave amplitude of the cardiac electrical signal.

In illustrative embodiments 6, the device of any of embodiments 1-5, wherein the control circuit is configured to determine each one of the first plurality of amplitudes by determining a cardiac event amplitude of the cardiac electrical signal during each one of a plurality of cardiac cycles.

In illustrative embodiments 7, the device of embodiments 1-6, wherein determining the first calibration relationship comprises determining at least one of a coefficient or a constant used for adjusting each of the second plurality of amplitudes.

In illustrative embodiments 8, the device of any of embodiments 1-7, wherein determining the first calibration relationship comprises generating a look-up table of calibrated cardiac electrical signal amplitudes.

In illustrative embodiments 9. The device of embodiments 1-8, wherein the control circuit is further configured to determine the calibration relationship by:
 determining the plurality of impedance metrics over a calibration time interval;
 determining the first plurality of cardiac electrical signal amplitudes during the calibration time interval;
 determining a range of the plurality of impedance metrics;
 extending the calibration time interval in response to the range of the plurality of impedance metrics being less than a minimum range; and
 determining the calibration relationship using the plurality of impedance metrics and the plurality of cardiac electrical signal amplitudes determined over the extended calibration time interval.

In illustrative embodiments 10, the device of any of embodiments embodiment 1-9, wherein the control circuit is further configured to generate a fluid status signal by:
 determining at least two impedance metrics from the impedance signal and spaced apart by a time interval;
 determining the second plurality of amplitudes of the cardiac electrical signal during the time interval; and
 generating a fluid status signal comprising at least one of the two impedance metrics and the adjusted second plurality of amplitudes of the cardiac electrical signal.

In illustrative embodiment 11, the device of any of embodiments 1-10, wherein the control circuit is further configured to:
 determine a verification impedance metric from the impedance signal after determining the second plurality of amplitudes from the cardiac electrical signal;
 determine a verification amplitude of the cardiac electrical signal corresponding in time to the verification impedance metric;
 adjust the verification amplitude of the cardiac electrical signal according to the first calibration relationship;
 compare the adjusted verification amplitude to the verification impedance metric; and
 re-determine the first calibration relationship in response to the adjusted verification amplitude being greater than a threshold difference from the verification impedance metric.

In illustrative embodiment 12, the device of any of embodiments 1-11, wherein the control circuit is further configured to:
 detect a threshold change in the adjusted second plurality of amplitudes; and
 re-determine the first calibration relationship in response to detecting the threshold change.

In illustrative embodiment 13, the device of any of embodiments 1-12, further comprising a posture sensor configured to produce a signal correlated to patient body posture and coupled to the control circuit;
 wherein the control circuit is further configured to:
 detect a change in patient body posture from the posture sensor signal, the change in patient body posture being from a first patient body posture corresponding to the first calibration relationship to a second patient body posture different than the first patient body posture;
 determine a second calibration relationship between the impedance signal and the cardiac electrical signal, the second calibration relationship corresponding to the second patient body posture;
 determine a third plurality of amplitudes of the cardiac electrical signal after the detected change in patient body posture; and
 generate the fluid status signal data by adjusting the third plurality of amplitudes according to the second calibration relationship.

In illustrative embodiment 14, the device of embodiment 13, wherein the control circuit is configured to determine the first calibration relationship using at least one impedance metric determined from the impedance signal after the detected change in patient body posture and an impedance metric determined from the impedance signal before the detected change in patient body posture.

In illustrative embodiment 15, the device of embodiments 13-14, wherein determining the first calibration relationship and the second calibration relationship by the control circuit comprises generating a look-up table comprising a first calibration parameter corresponding to the first patient body posture and a second calibration parameter corresponding to the second patient body posture.

In illustrative embodiment 16, the device of any of embodiments 13-15, wherein the control circuit is further configured to:
 generate a first fluid status signal comprising the adjusted second plurality of amplitudes corresponding to the first patient body posture; and
 generate a second fluid status signal comprising the adjusted third plurality of cardiac electrical signal amplitudes corresponding to the second patient body posture.

In illustrative embodiment 17, the device of any of embodiments 13-16, wherein the control circuit is further configured to generate the fluid status signal data by:
 updating the first calibration relationship each time the first patient body posture is detected;

adjusting cardiac electrical signal amplitudes that are acquired while the first patient body posture is being detected according to the first calibration relationship;

updating the second calibration relationship each time the second patient body posture is detected;

adjusting cardiac electrical signal amplitudes that are acquired while the second patient body posture is being detected according to the second calibration relationship;

generating a first fluid status signal by appending the cardiac electrical signal amplitudes adjusted according to the first calibration relationship;

generating a second fluid status signal by appending the cardiac electrical signal amplitudes adjusted according to the second calibration relationship;

wherein the first patient body posture comprises a plurality of upright patient body postures and the second patient body posture comprises a plurality of non-upright patient body postures.

In illustrative embodiment 18, the device of any of embodiments 1-12, further comprising a posture sensor configured to produce a signal correlated to patient body posture and coupled to the control circuit;

wherein the control circuit is further configured to:

detect a change in patient body posture from the posture sensor signal;

determine that the change in patient body posture is a major change in a center of gravity of the patient; and responsive to the change in patient body posture being a major change, determine a second calibration relationship between a second plurality of impedance metrics determined from the impedance signal and a third plurality of amplitudes of the cardiac electrical signal.

In illustrative embodiment 19, the device of any of embodiments 1-12, further comprising a posture sensor configured to produce a signal correlated to patient body posture and coupled to the control circuit;

wherein the control circuit is further configured to:

detect a change in patient body posture from the posture sensor signal;

determine whether the change in patient body posture is one of a major change in a center of gravity of the patient or a minor change in the center of gravity of the patient;

in response to the change in patient body posture being a major change, determining a second calibration relationship between the impedance signal and the cardiac electrical signal;

in response to the change in patient body posture being a minor change, determine when re-calibration criteria are met based on at least one of the impedance signal and the cardiac electrical signal; and determine a second calibration relationship between the impedance signal the cardiac electrical signal in response to the re-calibration criteria being met.

In illustrative embodiment 20, the device of any of embodiments 1-12, further comprising a posture sensor configured to produce a signal correlated to patient body posture and coupled to the control circuit;

wherein the control circuit is further configured to:

detect a change in patient body posture from the posture sensor signal;

generate fluid status signal data from the cardiac electrical signal after detecting the posture change; and determine a time response of a change in the fluid status signal data generated after detecting the change in patient body posture.

In illustrative embodiment 21, the device of embodiment 20, wherein the control circuit is configured to detect the change in patient body posture by detecting a change in patient body posture between an upright and a non-upright position.

In illustrative embodiment 22, the device of any of embodiments 1-21, further comprising a therapy circuit coupled to the control circuit and configured to deliver a therapy:

wherein the control circuit is further configured to:

compare the fluid status signal data to criteria for detecting a fluid status condition; and control the therapy circuit to adjust delivery of the therapy in response to the criteria for detecting a fluid status condition being met.

In illustrative embodiment, 23, the device of any of embodiments 1-22, wherein the control circuit is further configured to:

compare the fluid status signal data to criteria for detecting a fluid status condition; and generate an alert in response to the criteria for detecting a fluid status condition being met.

In illustrative embodiment 24, a method performed by an implantable medical device, the method comprising:

determining a plurality of impedance metrics from an impedance signal resulting from a drive signal applied to electrodes coupled to the medical device;

determining a first plurality of amplitudes from a cardiac electrical signal received by a sensing circuit via electrodes coupled to the medical device;

determining a first calibration relationship between the plurality of impedance metrics and the first plurality of amplitudes;

determining a second plurality of amplitudes from the cardiac electrical signal;

generating fluid status signal data by adjusting the second plurality of amplitudes according to the determined first calibration relationship; and transmitting the fluid status signal data to another medical device for generating a display of the fluid status signal data.

In illustrative embodiment 25, the method of embodiment 24, further comprising generating the drive signal from a power source coupled to the control circuit and the impedance sensing circuit, wherein the power source life is conserved by using the first calibration relationship compared to implantable medical devices that solely use the impedance signal to acquire fluid status signal data.

In illustrative embodiment 26, the method of any of embodiments 24-25, wherein determining each of the first plurality of amplitudes and the second plurality of amplitudes comprises determining an R-wave amplitude of the cardiac electrical signal.

In illustrative embodiment 27, the method of any of embodiments 24-26, wherein determining each one of the first plurality of amplitudes comprises determining a cardiac event amplitude of the cardiac electrical signal during each one of a plurality of cardiac cycles.

In illustrative embodiment 28, the method of any of embodiments 24-27, wherein determining the first calibration relationship comprises determining at least one of a coefficient or a constant used for adjusting each of the second plurality of amplitudes.

In illustrative embodiment 29, the method of any of embodiments 24-28, wherein determining the first calibration relationship comprises generating a look-up table of calibrated cardiac electrical signal amplitudes.

In illustrative embodiment 30, the method of any of embodiments 24-29, wherein determining the calibration relationship comprises:
  determining the plurality of impedance metrics over a calibration time interval;
  determining the first plurality of cardiac electrical signal amplitudes during the calibration time interval;
  determining a range of the plurality of impedance metrics;
  extending the calibration time interval in response to the range of the plurality of impedance metrics being less than a minimum range; and
  determining the calibration relationship using the plurality of impedance metrics and the plurality of cardiac electrical signal amplitudes determined over the extended calibration time interval.

In illustrative embodiment 31, the method of any of embodiments 24-30, further comprising generating a fluid status signal by:
  determining at least two impedance metrics from the impedance signal and spaced apart by a time interval;
  determining the second plurality of amplitudes of the cardiac electrical signal during the time interval; and
  generating the fluid status signal comprising at least one of the two impedance metrics and the adjusted second plurality of amplitudes of the cardiac electrical signal.

In illustrative embodiment 32, the method of any of embodiments 24-31, further comprising:
  determining a verification impedance metric from the impedance signal after determining the second plurality of amplitudes from the cardiac electrical signal;
  determining a verification amplitude of the cardiac electrical signal corresponding in time to the verification impedance metric;
  adjusting the verification amplitude of the cardiac electrical according to the first calibration relationship;
  comparing the adjusted verification amplitude to the verification impedance metric; and
  re-determining the first calibration relationship in response to the adjusted verification amplitude being greater than a threshold difference from the verification impedance metric.

In illustrative embodiment 33, the method of any of embodiments 24-32, further comprising:
  detecting a threshold change in the adjusted second plurality of amplitudes; and
  re-determine the first calibration relationship in response to detecting the threshold change.

In illustrative embodiment 34, the method of any of embodiments 24-33, further comprising:
  detecting a change in patient body posture from a posture sensor signal, the change in patient body posture being from a first patient body posture corresponding to the first calibration relationship to a second patient body posture different than the first patient body posture; and
  determining a second calibration relationship between the impedance signal and the cardiac electrical signal, the second calibration relationship corresponding to the second patient body posture
  determining a third plurality of amplitudes of the cardiac electrical signal after the detected change in patient body posture;
  wherein generating the fluid status signal data comprises adjusting the third plurality of amplitudes according to the second calibration relationship.

In illustrative embodiment 35, the method of embodiment 34, wherein the control circuit is configured to determine the first calibration relationship using at least one impedance metric determined from the impedance signal after the detected change in patient body posture and an impedance metric determined from the impedance signal before the detected change in patient body posture.

In illustrative embodiment 36, the method of any of embodiments 34-35, wherein determining the first calibration relationship and the second calibration relationship comprises generating a look-up table comprising a first calibration parameter corresponding to the first patient body posture and a second calibration parameter corresponding to the second patient body posture.

In illustrative embodiment 37, the method of any of embodiments 34-36, further comprising:
  generating a first fluid status signal comprising the adjusted second plurality of amplitudes corresponding to the first patient body posture; and
  generating a second fluid status signal comprising the adjusted third plurality of cardiac electrical signal amplitudes corresponding to the second patient body posture.

In illustrative embodiment 38, the method of any of embodiments 34-37, wherein generating the fluid status signal data comprises:
  updating the first calibration relationship each time the first patient body posture is detected;
  adjusting cardiac electrical signal amplitudes that are acquired while the first patient body posture is being detected according to the first calibration relationship;
  updating the second calibration relationship each time the second patient body posture is detected;
  adjusting cardiac electrical signal amplitudes that are acquired while the second patient body posture is being detected according to the second calibration relationship;
  generate a first fluid status signal by appending the cardiac electrical signal amplitudes adjusted according to the first calibration relationship;
  generate a second fluid status signal by appending the cardiac electrical signal amplitudes adjusted according to the second calibration relationship;
  wherein the first patient body posture comprises a plurality of upright patient body postures and the second patient body posture comprises a plurality of non-upright patient body postures.

In illustrative embodiment 39, the method of any of embodiments 24-33, further comprising:
  detecting a change in patient body posture from a posture sensor signal;
  determining that the change in patient body posture is a major change in a center of gravity of the patient; and
  responsive to the change in patient body posture being a major change, determining a second calibration relationship between a second plurality of impedance metrics determined from the impedance signal and a third plurality of amplitudes of the cardiac electrical signal.

In illustrative embodiment 40, the method of any of embodiments 24-33, further comprising:
  detecting a change in patient body posture from a posture sensor signal;
  determining whether the change in patient body posture is one of a major change in a center of gravity of the patient or a minor change in the center of gravity of the patient;
  in response to the change in patient body posture being a major change, determining a second calibration relationship between the impedance signal and the cardiac electrical signal;

in response to the change in patient body posture being a minor change, determine when re-calibration criteria are met based on at least one of the impedance signal and the cardiac electrical signal; and determine a second calibration relationship between the impedance signal the cardiac electrical signal in response to the re-calibration criteria being met.

In illustrative embodiment 41, the method of any of embodiments 24-33, further comprising:

detecting a change in patient body posture from the posture sensor signal;

generating fluid status signal data from the cardiac electrical signal after detecting the posture change; and determining a time response of a change in the fluid status signal data generated after detecting the change in patient body posture.

In illustrative embodiment 42, the method of embodiment 41, wherein detecting the change in patient body posture comprises detecting a change in patient body posture between an upright and a non-upright position.

In illustrative embodiment 43, the method of any of embodiments 24-42, further comprising:

comparing the fluid status signal data to criteria for detecting a fluid status condition; and control a therapy circuit to adjust delivery of a therapy in response to the criteria for detecting a fluid status condition being met.

In illustrative embodiment 44, the method of any of embodiments 24-43, further comprising:

comparing the fluid status signal data to criteria for detecting a fluid status condition; and generating an alert in response to the criteria for detecting a fluid status condition being met.

In illustrative embodiment 45, A non-transitory computer-readable medium storing a set of instructions which when executed by a control circuit of a medical device, cause the medical device to:

determine a plurality of impedance metrics from an impedance signal resulting from a drive signal applied to electrodes coupled to the medical device;

determine a first plurality of amplitudes from a cardiac electrical signal received by a sensing circuit via electrodes coupled to the medical device;

determine a calibration relationship between the plurality of impedance metrics and the first plurality of amplitudes;

determine a second plurality of amplitudes from the cardiac electrical signal;

generate fluid status signal data by adjusting the second plurality of amplitudes according to the determined first calibration relationship; and transmit the fluid status signal data to another medical device for displaying the fluid status signal data.

In illustrative embodiment 46, an implantable medical device system, comprising:

an external device comprising a display unit and a telemetry unit;

an implantable medical device comprising:

a housing;

at least one housing-based electrode;

a sensing circuit configured to receive a cardiac electrical signal via an electrode pair comprising at least one electrode carried by a medical lead coupled to the medical device and the housing-based electrode;

an impedance sensing circuit configured to apply a drive signal to the at least one housing-based electrode and sense a resultant impedance signal;

a telemetry circuit configured to transmit fluid status data to the external medical device; and a control circuit coupled to the sensing circuit, the impedance sensing circuit and the telemetry circuit, the control circuit configured to:

determine a plurality of impedance metrics from the impedance signal at spaced apart time points;

determine a first plurality of amplitudes from the cardiac electrical signal at spaced apart time points;

determine a calibration relationship between at least a portion of the plurality of impedance metrics and the first plurality of amplitudes;

determine a second plurality of amplitudes from the cardiac electrical signal at spaced apart time intervals;

generate fluid status signal data by adjusting the second plurality of amplitudes according to the determined calibration relationship; and control the telemetry circuit to transmit the fluid status signal data to the external device;

wherein the external device is configured to generate a display of a fluid status signal from the fluid status signal data, the fluid status signal comprising at least a first impedance metric of the plurality of impedance metrics plotted at a corresponding first time point, a second impedance metric of the plurality of impedance metrics plotted at a corresponding second time point, and the second plurality of amplitudes adjusted according to the determined first calibration relationship each plotted at respective time points intervening the first time point and the second time point.

In illustrative embodiment 47, a medical device, comprising:

a telemetry circuit configured to receive fluid status data from another medical device, the fluid status data comprising a plurality of cardiac electrical signal amplitudes and a plurality of impedance metrics; and a control circuit coupled to the telemetry circuit and configured to:

determine a calibration relationship between the plurality of impedance metrics and the plurality of cardiac signal amplitudes;

adjust the plurality of cardiac electrical signal amplitudes according to the determined calibration relationship; and generate a fluid status signal comprising the adjusted cardiac electrical signal amplitudes;

compare the fluid status signal to at least one threshold;

determining a therapy adjustment command based on the comparison; and transmitting the therapy adjustment command to a therapy delivery device for delivering a therapy to a patient according to the therapy adjustment command.

Thus, a medical device for monitoring a patient's fluid status has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

The invention claimed is:

1. A medical device, comprising:

a sensing circuit configured to receive a cardiac electrical signal via electrodes coupled to the medical device;

an impedance sensing circuit configured to apply a drive signal to electrodes coupled to the medical device and sense a resultant impedance signal;

a telemetry circuit configured to transmit fluid status data to another medical device; and a control circuit coupled to the sensing circuit, the impedance sensing circuit and the telemetry circuit, the control circuit configured to:
- determine a plurality of impedance metrics from the impedance signal;
- determine a first plurality of amplitudes from the cardiac electrical signal;
- determine a first calibration relationship between the plurality of impedance metrics and the first plurality of amplitudes;
- determine a second plurality of amplitudes from the cardiac electrical signal; and
- generate fluid status signal data by adjusting the second plurality of amplitudes according to the determined first calibration relationship.

2. The device of claim 1, further comprising a power source coupled to the control circuit and the impedance sensing circuit for generating the drive signal, wherein the power source life is conserved by using the first calibration relationship compared to implantable medical devices that solely use the impedance signal to acquire fluid status signal data.

3. The device of claim 2, wherein the power source is a battery.

4. The device of claim 1, wherein the control circuit is further configured to control the telemetry circuit to transmit the fluid status signal data to another medical device for generating a display of the fluid status signal data.

5. The device of claim 1, wherein the control circuit is configured to determine each of the first plurality of amplitudes and each of the second plurality of amplitudes by determining an R-wave amplitude of the cardiac electrical signal.

6. The device of claim 1, wherein the control circuit is configured to determine each one of the first plurality of amplitudes by determining a cardiac event amplitude of the cardiac electrical signal during each one of a plurality of cardiac cycles.

7. The device of claim 1, wherein determining the first calibration relationship comprises determining at least one of a coefficient or a constant used for adjusting each of the second plurality of amplitudes.

8. The device of claim 1, wherein determining the first calibration relationship comprises generating a look-up table of calibrated cardiac electrical signal amplitudes.

9. The device of claim 1, wherein the control circuit is further configured to determine the calibration relationship by:
- determining the plurality of impedance metrics over a calibration time interval;
- determining the first plurality of cardiac electrical signal amplitudes during the calibration time interval;
- determining a range of the plurality of impedance metrics;
- extending the calibration time interval in response to the range of the plurality of impedance metrics being less than a minimum range; and
- determining the calibration relationship using the plurality of impedance metrics and the plurality of cardiac electrical signal amplitudes determined over the extended calibration time interval.

10. The device of claim 1, wherein the control circuit is further configured to generate a fluid status signal by:
- determining at least two impedance metrics from the impedance signal and spaced apart by a time interval;
- determining the second plurality of amplitudes of the cardiac electrical signal during the time interval; and
- generating a fluid status signal comprising at least one of the two impedance metrics and the adjusted second plurality of amplitudes of the cardiac electrical signal.

11. The device of claim 1, wherein the control circuit is further configured to:
- determine a verification impedance metric from the impedance signal after determining the second plurality of amplitudes from the cardiac electrical signal;
- determine a verification amplitude of the cardiac electrical signal corresponding in time to the verification impedance metric;
- adjust the verification amplitude of the cardiac electrical according to the first calibration relationship;
- compare the adjusted verification amplitude to the verification impedance metric; and
- re-determine the first calibration relationship in response to the adjusted verification amplitude being greater than a threshold difference from the verification impedance metric.

12. The device of claim 1, wherein the control circuit is further configured to:
- detect a threshold change in the adjusted second plurality of amplitudes; and
- re-determine the first calibration relationship in response to detecting the threshold change.

13. The device of claim 1, further comprising a posture sensor configured to produce a signal correlated to patient body posture and coupled to the control circuit;
wherein the control circuit is further configured to:
- detect a change in patient body posture from the posture sensor signal, the change in patient body posture being from a first patient body posture corresponding to the first calibration relationship to a second patient body posture different than the first patient body posture;
- determine a second calibration relationship between the impedance signal and the cardiac electrical signal, the second calibration relationship corresponding to the second patient body posture;
- determine a third plurality of amplitudes of the cardiac electrical signal after the detected change in patient body posture; and
- generate the fluid status signal data by adjusting the third plurality of amplitudes according to the second calibration relationship.

14. The device of claim 13, wherein the control circuit is configured to determine the first calibration relationship using at least one impedance metric determined from the impedance signal after the detected change in patient body posture and an impedance metric determined from the impedance signal before the detected change in patient body posture.

15. The device of claim 13, wherein determining the first calibration relationship and the second calibration relationship by the control circuit comprises generating a look-up table comprising a first calibration parameter corresponding to the first patient body posture and a second calibration parameter corresponding to the second patient body posture.

16. The device of claim 13, wherein the control circuit is further configured to:
- generate a first fluid status signal comprising the adjusted second plurality of amplitudes corresponding to the first patient body posture; and generate a second fluid status signal comprising the adjusted third plurality of cardiac electrical signal amplitudes corresponding to the second patient body posture.

17. The device of claim 13, wherein the control circuit is further configured to generate the fluid status signal data by:
updating the first calibration relationship each time the first patient body posture is detected;
adjusting cardiac electrical signal amplitudes that are acquired while the first patient body posture is being detected according to the first calibration relationship;
updating the second calibration relationship each time the second patient body posture is detected;
adjusting cardiac electrical signal amplitudes that are acquired while the second patient body posture is being detected according to the second calibration relationship;
generating a first fluid status signal by appending the cardiac electrical signal amplitudes adjusted according to the first calibration relationship;
generating a second fluid status signal by appending the cardiac electrical signal amplitudes adjusted according to the second calibration relationship;
wherein the first patient body posture comprises a plurality of upright patient body postures and the second patient body posture comprises a plurality of non-upright patient body postures.

18. The device of claim 1, further comprising a posture sensor configured to produce a signal correlated to patient body posture and coupled to the control circuit;
wherein the control circuit is further configured to:
detect a change in patient body posture from the posture sensor signal;
determine that the change in patient body posture is a major change in a center of gravity of the patient; and
responsive to the change in patient body posture being a major change, determine a second calibration relationship between a second plurality of impedance metrics determined from the impedance signal and a third plurality of amplitudes of the cardiac electrical signal.

19. The device of claim 1, further comprising a posture sensor configured to produce a signal correlated to patient body posture and coupled to the control circuit;
wherein the control circuit is further configured to:
detect a change in patient body posture from the posture sensor signal;
determine whether the change in patient body posture is one of a major change in a center of gravity of the patient or a minor change in the center of gravity of the patient;
in response to the change in patient body posture being a major change, determining a second calibration relationship between the impedance signal and the cardiac electrical signal;
in response to the change in patient body posture being a minor change, determine when re-calibration criteria are met based on at least one of the impedance signal and the cardiac electrical signal; and
determine a second calibration relationship between the impedance signal the cardiac electrical signal in response to the re-calibration criteria being met.

20. The device of claim 1, further comprising a posture sensor configured to produce a signal correlated to patient body posture and coupled to the control circuit;

wherein the control circuit is further configured to:
detect a change in patient body posture from the posture sensor signal;
generate fluid status signal data from the cardiac electrical signal after detecting the posture change; and
determine a time response of a change in the fluid status signal data generated after detecting the change in patient body posture.

21. The device of claim 20, wherein the control circuit is configured to detect the change in patient body posture by detecting a change in patient body posture between an upright and a non-upright position.

22. The device of claim 1, further comprising a therapy circuit coupled to the control circuit and configured to deliver a therapy:
wherein the control circuit is further configured to:
compare the fluid status signal data to criteria for detecting a fluid status condition; and
control the therapy circuit to adjust delivery of the therapy in response to the criteria for detecting a fluid status condition being met.

23. The device of claim 1, wherein the control circuit is further configured to:
compare the fluid status signal data to criteria for detecting a fluid status condition; and
generate an alert in response to the criteria for detecting a fluid status condition being met.

24. A method performed by an implantable medical device, the method comprising:
determining a plurality of impedance metrics from an impedance signal resulting from a drive signal applied to electrodes coupled to the medical device;
determining a first plurality of amplitudes from a cardiac electrical signal received by a sensing circuit via electrodes coupled to the medical device;
determining a first calibration relationship between the plurality of impedance metrics and the first plurality of amplitudes;
determining a second plurality of amplitudes from the cardiac electrical signal;
generating fluid status signal data by adjusting the second plurality of amplitudes according to the determined first calibration relationship; and
transmitting the fluid status signal data to another medical device for generating a display of the fluid status signal data.

25. The method of claim 24, further comprising generating the drive signal from a power source coupled to the control circuit and the impedance sensing circuit, wherein the power source life is conserved by using the first calibration relationship compared to implantable medical devices that solely use the impedance signal to acquire fluid status signal data.

26. The method of claim 24, wherein determining each of the first plurality of amplitudes and the second plurality of amplitudes comprises determining an R-wave amplitude of the cardiac electrical signal.

27. The method of claim 24, wherein determining each one of the first plurality of amplitudes comprises determining a cardiac event amplitude of the cardiac electrical signal during each one of a plurality of cardiac cycles.

28. The method of claim 24, wherein determining the first calibration relationship comprises determining at least one of a coefficient or a constant used for adjusting each of the second plurality of amplitudes.

29. The method of claim 24, wherein determining the first calibration relationship comprises generating a look-up table of calibrated cardiac electrical signal amplitudes.

30. The method of claim 24, wherein determining the calibration relationship comprises:
   determining the plurality of impedance metrics over a calibration time interval;
   determining the first plurality of cardiac electrical signal amplitudes during the calibration time interval;
   determining a range of the plurality of impedance metrics;
   extending the calibration time interval in response to the range of the plurality of impedance metrics being less than a minimum range; and
   determining the calibration relationship using the plurality of impedance metrics and the plurality of cardiac electrical signal amplitudes determined over the extended calibration time interval.

31. The method of claim 24, further comprising generating a fluid status signal by:
   determining at least two impedance metrics from the impedance signal and spaced apart by a time interval;
   determining the second plurality of amplitudes of the cardiac electrical signal during the time interval; and
   generating the fluid status signal comprising at least one of the two impedance metrics and the adjusted second plurality of amplitudes of the cardiac electrical signal.

32. The method of claim 24, further comprising:
   determining a verification impedance metric from the impedance signal after determining the second plurality of amplitudes from the cardiac electrical signal;
   determining a verification amplitude of the cardiac electrical signal corresponding in time to the verification impedance metric;
   adjusting the verification amplitude of the cardiac electrical according to the first calibration relationship;
   comparing the adjusted verification amplitude to the verification impedance metric; and
   re-determining the first calibration relationship in response to the adjusted verification amplitude being greater than a threshold difference from the verification impedance metric.

33. The method of claim 24, further comprising:
   detecting a threshold change in the adjusted second plurality of amplitudes; and
   re-determine the first calibration relationship in response to detecting the threshold change.

34. The method of claim 24, further comprising:
   detecting a change in patient body posture from a posture sensor signal, the change in patient body posture being from a first patient body posture corresponding to the first calibration relationship to a second patient body posture different than the first patient body posture; and
   determining a second calibration relationship between the impedance signal and the cardiac electrical signal, the second calibration relationship corresponding to the second patient body posture
   determining a third plurality of amplitudes of the cardiac electrical signal after the detected change in patient body posture;
   wherein generating the fluid status signal data comprises adjusting the third plurality of amplitudes according to the second calibration relationship.

35. The method of claim 34, wherein the control circuit is configured to determine the first calibration relationship using at least one impedance metric determined from the impedance signal after the detected change in patient body posture and an impedance metric determined from the impedance signal before the detected change in patient body posture.

36. The method of claim 34, wherein determining the first calibration relationship and the second calibration relationship comprises generating a look-up table comprising a first calibration parameter corresponding to the first patient body posture and a second calibration parameter corresponding to the second patient body posture.

37. The method of claim 34, further comprising:
   generating a first fluid status signal comprising the adjusted second plurality of amplitudes corresponding to the first patient body posture; and
   generating a second fluid status signal comprising the adjusted third plurality of cardiac electrical signal amplitudes corresponding to the second patient body posture.

38. The method of claim 34, wherein generating the fluid status signal data comprises:
   updating the first calibration relationship each time the first patient body posture is detected;
   adjusting cardiac electrical signal amplitudes that are acquired while the first patient body posture is being detected according to the first calibration relationship;
   updating the second calibration relationship each time the second patient body posture is detected;
   adjusting cardiac electrical signal amplitudes that are acquired while the second patient body posture is being detected according to the second calibration relationship;
   generate a first fluid status signal by appending the cardiac electrical signal amplitudes adjusted according to the first calibration relationship;
   generate a second fluid status signal by appending the cardiac electrical signal amplitudes adjusted according to the second calibration relationship;
   wherein the first patient body posture comprises a plurality of upright patient body postures and the second patient body posture comprises a plurality of non-upright patient body postures.

39. The method of claim 24, further comprising:
   detecting a change in patient body posture from a posture sensor signal;
   determining that the change in patient body posture is a major change in a center of gravity of the patient; and
   responsive to the change in patient body posture being a major change, determining a second calibration relationship between a second plurality of impedance metrics determined from the impedance signal and a third plurality of amplitudes of the cardiac electrical signal.

40. The method of any of claim 24, further comprising:
   detecting a change in patient body posture from a posture sensor signal;
   determining whether the change in patient body posture is one of a major change in a center of gravity of the patient or a minor change in the center of gravity of the patient;
   in response to the change in patient body posture being a major change, determining a second calibration relationship between the impedance signal and the cardiac electrical signal;
   in response to the change in patient body posture being a minor change, determine when re-calibration criteria are met based on at least one of the impedance signal and the cardiac electrical signal; and determine a second calibration relationship between the impedance signal the cardiac electrical signal in response to the re-calibration criteria being met.

41. The method of claim 24, further comprising:
    detecting a change in patient body posture from the posture sensor signal;
    generating fluid status signal data from the cardiac electrical signal after detecting the posture change; and
    determining a time response of a change in the fluid status signal data generated after detecting the change in patient body posture.

42. The method of claim 41, wherein detecting the change in patient body posture comprises detecting a change in patient body posture between an upright and a non-upright position.

43. The method of claim 24, further comprising:
    comparing the fluid status signal data to criteria for detecting a fluid status condition; and
    control a therapy circuit to adjust delivery of a therapy in response to the criteria for detecting a fluid status condition being met.

44. The method of claim 24, further comprising:
    comparing the fluid status signal data to criteria for detecting a fluid status condition; and
    generating an alert in response to the criteria for detecting a fluid status condition being met.

45. A non-transitory computer-readable medium storing a set of instructions which when executed by a control circuit of a medical device, cause the medical device to:
    determine a plurality of impedance metrics from an impedance signal resulting from a drive signal applied to electrodes coupled to the medical device;
    determine a first plurality of amplitudes from a cardiac electrical signal received by a sensing circuit via electrodes coupled to the medical device;
    determine a calibration relationship between the plurality of impedance metrics and the first plurality of amplitudes;
    determine a second plurality of amplitudes from the cardiac electrical signal;
    generate fluid status signal data by adjusting the second plurality of amplitudes according to the determined first calibration relationship; and
    transmit the fluid status signal data to another medical device for displaying the fluid status signal data.

46. A medical device, comprising:
    a telemetry circuit configured to receive fluid status data from another medical device, the fluid status data comprising a plurality of cardiac electrical signal amplitudes and a plurality of impedance metrics; and
    a control circuit coupled to the telemetry circuit and configured to:
        determine a calibration relationship between the plurality of impedance metrics and the plurality of cardiac signal amplitudes;
        adjust the plurality of cardiac electrical signal amplitudes according to the determined calibration relationship; and
        generate a fluid status signal comprising the adjusted cardiac electrical signal amplitudes;
        compare the fluid status signal to at least one threshold;
        determining a therapy adjustment command based on the comparison; and
        transmitting the therapy adjustment command to a therapy delivery device for delivering a therapy to a patient according to the therapy adjustment command.

* * * * *